(12) United States Patent
Whiting et al.

(10) Patent No.: US 10,759,762 B2
(45) Date of Patent: Sep. 1, 2020

(54) FLUORESCENT SYNTHETIC RETINOIDS

(71) Applicant: High Force Research Limited, Durham (GB)

(72) Inventors: Andrew Whiting, Durham (GB); Todd Marder, Würzburg (DE)

(73) Assignee: HIGH FORCE RESEARCH LIMITED, Durham (GB)

( * ) Notice: Subject to any disclaimer, the term of this patent is extended or adjusted under 35 U.S.C. 154(b) by 0 days.

(21) Appl. No.: 15/514,923

(22) PCT Filed: Oct. 9, 2015

(86) PCT No.: PCT/GB2015/052956
§ 371 (c)(1),
(2) Date: Mar. 28, 2017

(87) PCT Pub. No.: WO2016/055800
PCT Pub. Date: Apr. 14, 2016

(65) Prior Publication Data
US 2017/0217893 A1    Aug. 3, 2017

(30) Foreign Application Priority Data

Oct. 10, 2014  (GB) ................................. 1417957.6
Oct. 31, 2014  (GB) ................................. 1419496.3

(51) Int. Cl.
| | | |
|---|---|---|
| *C07D 215/06* | (2006.01) | |
| *C12N 5/095* | (2010.01) | |
| *G01N 33/50* | (2006.01) | |

(52) U.S. Cl.
CPC ......... *C07D 215/06* (2013.01); *C12N 5/0695* (2013.01); *G01N 33/5011* (2013.01); *G01N 33/5073* (2013.01); *C12N 2501/999* (2013.01); *G01N 2500/04* (2013.01); *G01N 2500/10* (2013.01)

(58) Field of Classification Search
CPC .................................................. C07D 215/06
See application file for complete search history.

(56) References Cited

U.S. PATENT DOCUMENTS

| | | | | |
|---|---|---|---|---|
| 4,678,793 A | * | 7/1987 | Klaus ................... | C07D 215/06 514/311 |
| 4,810,804 A | | 3/1989 | Chandraratna | |
| 4,980,369 A | | 12/1990 | Chandraratna | |
| 5,023,341 A | | 6/1991 | Chandraratna | |
| 5,324,840 A | * | 6/1994 | Chandraratna ...... | C07D 213/80 546/318 |
| 6,387,951 B1 | | 5/2002 | Vasudevan et al. | |
| 6,906,057 B1 | * | 6/2005 | Forman ................. | A61K 31/55 514/211.08 |
| 7,468,391 B2 | * | 12/2008 | Vasudevan ............ | A61K 31/19 424/400 |
| 2007/0078160 A1 | | 4/2007 | Lagu et al. | |

FOREIGN PATENT DOCUMENTS

| | | | |
|---|---|---|---|
| CN | 101316821 | | 12/2008 |
| EP | 0130795 | * | 1/1985 |
| EP | 0130795 A | | 1/1985 |
| EP | 0130795 A2 | | 1/1985 |
| JP | S58206567 | | 12/1983 |
| JP | S6036461 | | 2/1985 |
| JP | S63264578 | | 11/1988 |
| JP | H03120273 | | 5/1991 |
| JP | H03167174 | | 7/1991 |
| JP | H07503733 | | 4/1995 |
| JP | H08505852 | | 6/1996 |
| JP | 2004505519 | | 2/2004 |
| JP | 2004-507531 | | 3/2004 |
| JP | 2010503615 | | 2/2010 |
| JP | 2014527083 | | 10/2014 |
| WO | 93/16068 | | 8/1993 |
| WO | 94/15902 | | 7/1994 |
| WO | 97/12853 | | 4/1997 |
| WO | 98/07716 | * | 2/1998 |
| WO | 00/59861 | | 10/2000 |
| WO | 02/18361 A2 | | 3/2002 |

(Continued)

OTHER PUBLICATIONS

Beard et al., "Synthesis and biological activity of 1,2,3,4-tetrahydroquinoline and 3,4-(1H)-dihydroquinolin-2-one analogs of retinoic acid," Biorganic & Medicinal Chemistry Letters, 7(18):2373-2378, Sep. 23, 1997.
PCT International Search Report for International Application No. PCT/GB2015/052956, dated Apr. 28, 2016, 4 pages.
PCT Written Opinion of the International Searching Authority for International Application No. PCT/GB2015/052956, dated Apr. 28, 2016, 7 pages.
PCT International Search Report of International Searching Authority for International Patent Application PCT/US01/25443, 9 pages.
CAS RN 1575541-43-3; STN entry date: Mar. 28, 2014 4-[[(1-Acetyl-1,2,3,4-tetrahydro-6-quinolinyl)carbonyl]amino]-benzoic acid.
CAS RN 1147235-48-0; STN entry date: May 19, 2009 4-[[(1-Benzoyl-1,2,3,4-tetrahydro-6-quinolinyl)carbonyl]amino]-benzoic acid methyl ester.

(Continued)

*Primary Examiner* — D Margaret M Seaman
(74) *Attorney, Agent, or Firm* — K&L Gates LLP

(57) ABSTRACT

There are described novel compounds of formula I: which $R^1$, $R^2$, $R^3$, $R^4$, $R^5$, $R^6$, $R^7$, $R^8$, $R^9$ and $R^{10}$ are each as herein defined.

(I)

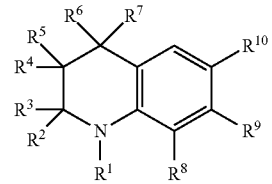

13 Claims, 18 Drawing Sheets

(56) References Cited

FOREIGN PATENT DOCUMENTS

| WO | 2008/025965 | 3/2008 |
|----|-------------|--------|
| WO | 2008/025965 A2 | 3/2008 |
| WO | 2013/040227 | 3/2013 |

OTHER PUBLICATIONS

CAS RN 1347651-75-5; STN entry date: Dec. 2, 2011 4-[2-(1-Cyclopentyl-1,2,3,4-tetrahydro-4,4-dimethyl-6-quinolinyl)ethynyl]-benzoic acid.

CAS RN 1051343-41-9; STN entry date: Sep. 22, 2008 3-[[[1,2,3,4-Tetrahydro-1-(methylsulfonyl)-6-quinolinyl] carbonyl]amino]-benzoic acid.

CAS RN 1051179-57-7; STN entry date: Sep. 21, 2008 4-[[[1,2,3,4-Tetrahydro-1-(methylsulfonyl)-6-quinolinyl] carbonyl]amino]-benzoic acid.

Thacher et al., "Therapeutic Applications for Ligands of Retinoid Receptors," Current Pharmaceutical Design, 2000, 6, pp. 25-58.

Zhou et al., "Synthesis and applications of 2,4-disubstituted thiazole derivatives as small molecule modulators of ellular development", Organic and Biomolecular Chemistry, 2013, 11(14), pp. 2323-2334.

CAS RN 1369458-98-9; STN entry date: Apr. 17, 2012, 3-[3-(1,2,3,4-tetrahydro-1-methyl-6-quinohnyl)phenyl]-2-butenoic acid.

CAS RN 1028306-88-8; STN entry date: Jun. 15, 2008, 4-[2-(1-cyclopropyl-1,2,3,4-tetrahydro-4,4-dimethyl-6-quinolinyl)ethynyl]-benzoic acid methyl ester.

* cited by examiner

Normalised excitation spectra of EC23® in a range of solvents.

Normalised emission spectra of EC23® in a range of solvents, with excitation at 300 nm.

Normalised excitation spectra of compound 9 in a range of solvents.

Normalised emission spectra of compound 9 in a range of solvents, with excitation in the range of 275-300 nm.

Normalised excitation spectrum of compound 17 in chloroform.

Normalised emission spectrum of compound 17 in chloroform, with excitation at 378 nm.

$^1$H NMR spectrum of compound 9 in DMSO-$d_6$ before exposure to light of a wavelength of 300-400 nm.

$^1$H NMR spectrum of compound 9 in DMSO-$d_6$ after 72 hour exposure to light of a wavelength of 300-400 nm.

| | 1 µM treatment | 10 µM treatment |
|---|---|---|
| ATRA | | |
| EC23® | | |
| Compound 9 | | |
| DMSO | | Nestin is an intermediate filament expressed in neural stem cells.<br><br>All conditions positive for nestin with staining possibly to a lesser extent in 10 µM EC23® and DC271 samples. |

Compound 9 activity in stem cells compared to ATRA, EC23® and DMSO - Nestin staining.

FIG. 9

Compound 9 activity in stem cells compared to ATRA, EC23® and DMSO – TUJ-1 staining.

Compound 9 activity in stem cells compared to ATRA, EC23® and DMSO – Oct 4 staining.

|  | 1 μM treatment | 10 μM treatment |
|---|---|---|
| ATRA | | |
| EC23® | | |
| Compound 9 | | |
| DMSO | | Sox 2 is a transcription factor that is a marker of pluripotency. The vehicle control (DMSO) demonstrates positive staining for the nuclear factor, with reduced staining with all conditions. This suggests that EC23® and compound 9 retinoids readily down regulate markers of pluripotency, through promoting differentiation. |

Compound 9 activity in stem cells compared to ATRA, EC23® and DMSO – Sox 2 staining.

FIG. 13

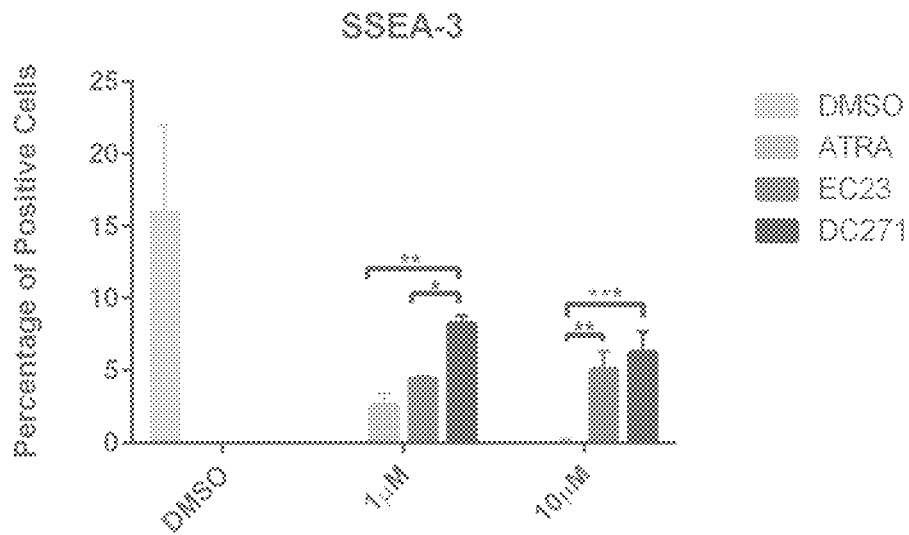

Flow cytometry evaluation of compound 9 (DC271) compared to ATRA, EC23® and DMSO. The expression of stem cell marker SSEA-3 is measured. SSEA3 expression is significantly decreased in retinoid treated cells when compared to the vehicle control (DMSO). Compound 9 (DC271) treated cells show higher levels of SSEA-3 than ATRA and EC23® at both treatments concentrations. Generally SSEA-3 expression is reduced with increasing retinoid concentration.

FIG. 14

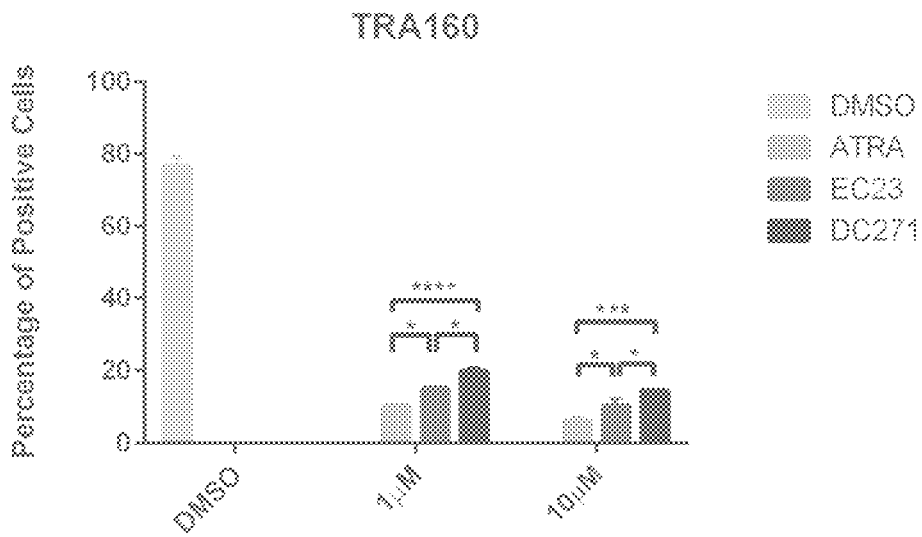

Flow cytometry evaluation of compound 9 (DC271) compared to ATRA, EC23® and DMSO. The expression of stem cell marker TRA160 is measured. TRA160 expression is significantly decreased in retinoid treated cells when compared to the vehicle control (DMSO). Compound 9 (DC271) treated cells exhibit slightly higher expression of TRA160 than ATRA and EC23®. Generally TRA160 expression is reduced with increasing retinoid concentration.

FIG. 15

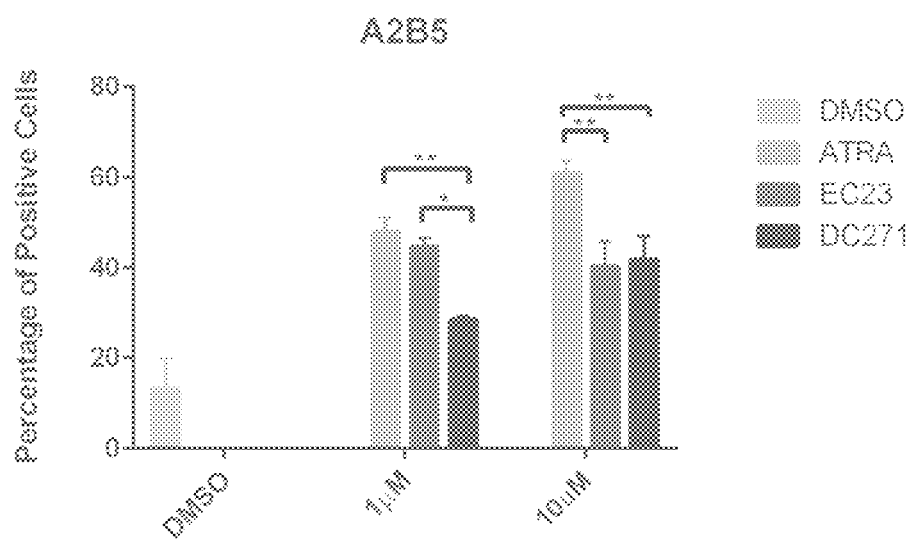

Flow cytometry evaluation of compound 9 (DC271) compared to ATRA, EC23® and DMSO. The expression of stem cell marker A2B5 is measured. A2B5 is an early neuronal marker and is expressed at low levels in undifferentiated cells (DMSO). Expression is significantly enhanced in retinoid treated samples and increases with increasing retinoid concentration. ATRA treated cells express higher levels of A2B5 followed by EC23® and compound 9 (DC271).

FIG. 16

| | 1 μM treatment | 10 μM treatment |
|---|---|---|
| ATRA | 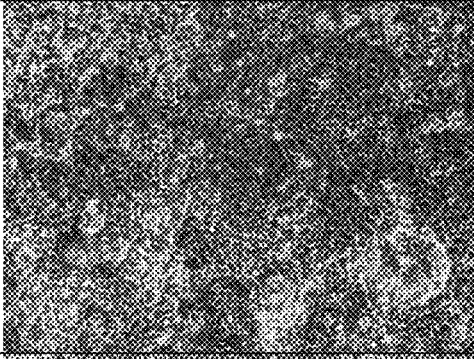 | 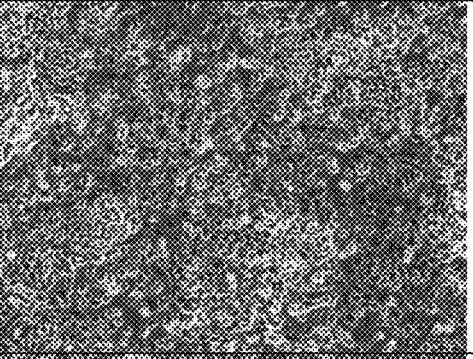 |
| EC23® | 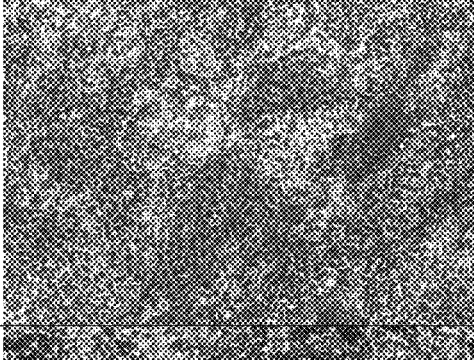 | 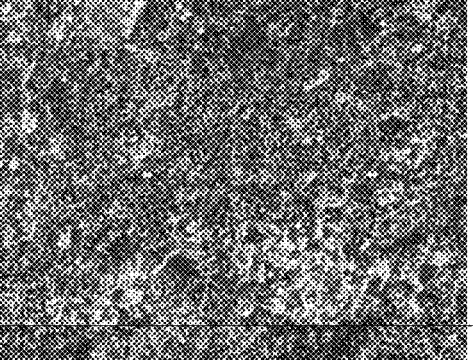 |
| Compound 9 | 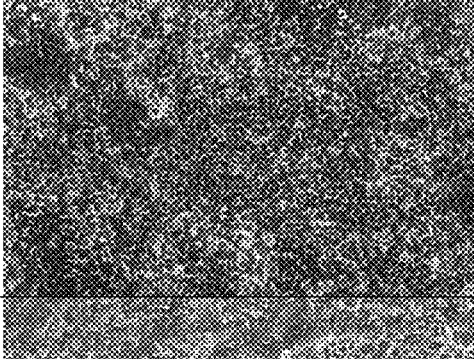 | 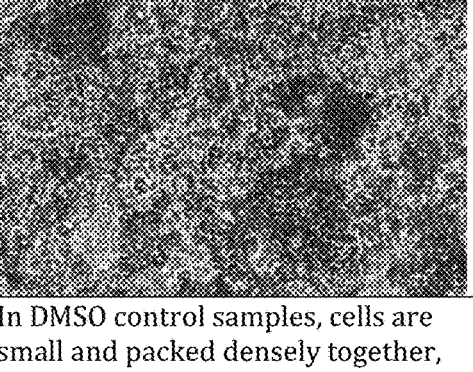 |
| DMSO | 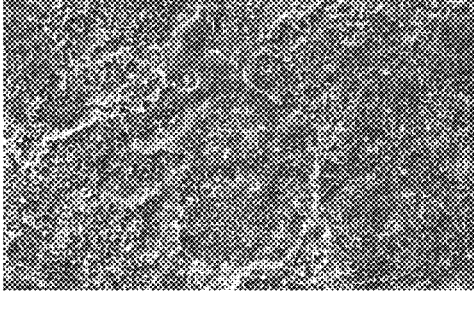 | In DMSO control samples, cells are small and packed densely together, whereas in samples treated with compound 9 and ATRA/EC23®, cells are spread out and cultures are less dense. |
Phase contrast images of cell populations treated with compound 9, ATRA, EC23® and DMSO.
FIG. 17

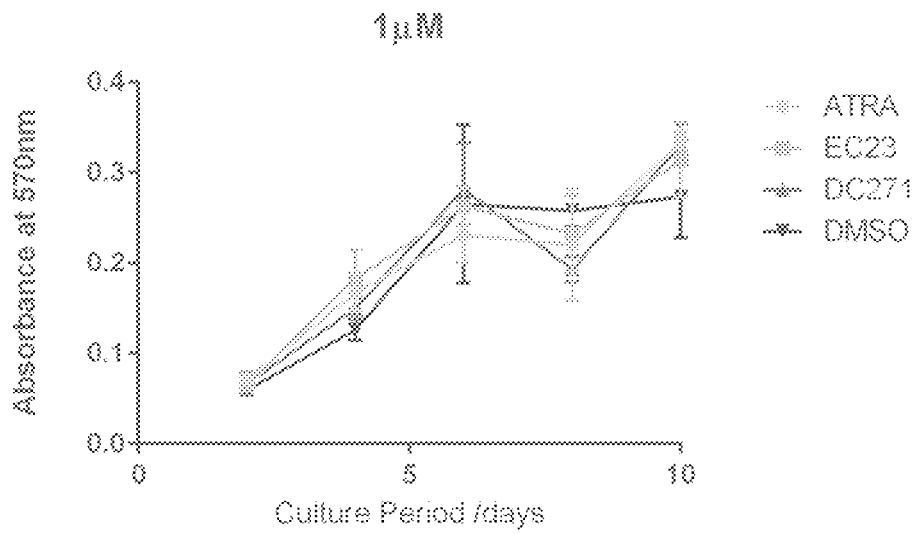

MTT cell viability analysis of compound 9 (DC271) with comparison to ATRA, EC23® and DMSO at a treatment concentration of 1 μM. All treatments exhibit comparable viability to DMSO, suggesting cells treated with retinoids do not experience significant toxic effects.

FIG. 18

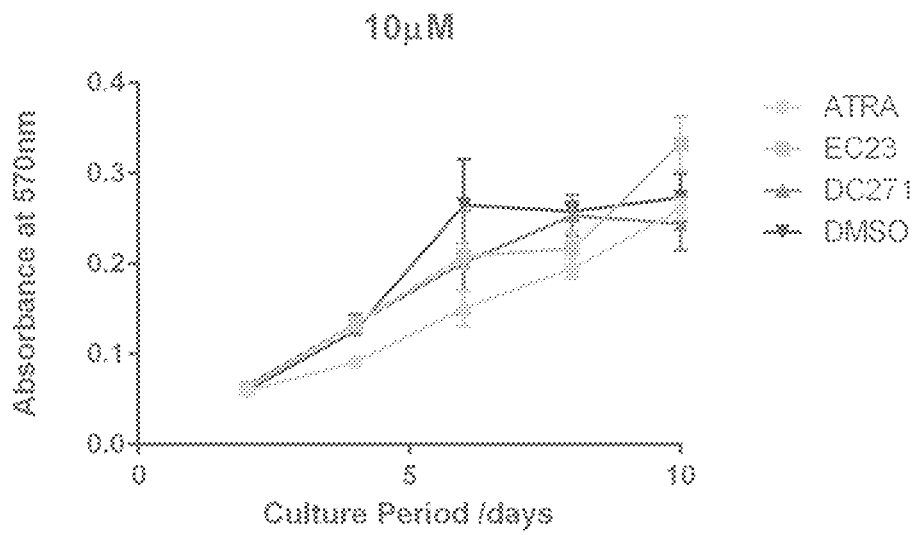

MTT cell viability analysis of compound 9 (DC271), with comparison to ATRA, EC23® and DMSO at a treatment concentration of 10 μM. All treatments exhibit comparable viability to DMSO, suggesting cells treated with retinoids do not experience significant toxic effects.

FIG. 19

TERA-2 stem cells treated with compound 9 over a range of concentrations, imaged using confocal microscope after 7 days.

SHSY5Y cells (neuroblastoma) treated with compound 9 (10 µM), and imaged using a confocal microscope after 8 hours.

Fibroblast cells treated with compound 9 (10 µM), and imaged using a confocal microscope after 24 hours.

TERA-2 stem cells treated with compound 9 (10 µM) for 7 days, fixed with 4% paraformaldehyde, and imaged using a confocal microscope.

HaCat keratinocyte skin cells treated with compound 9 (10 µM) for 5 days, fixed and then imaged with a confocal microscope.

FIG. 24

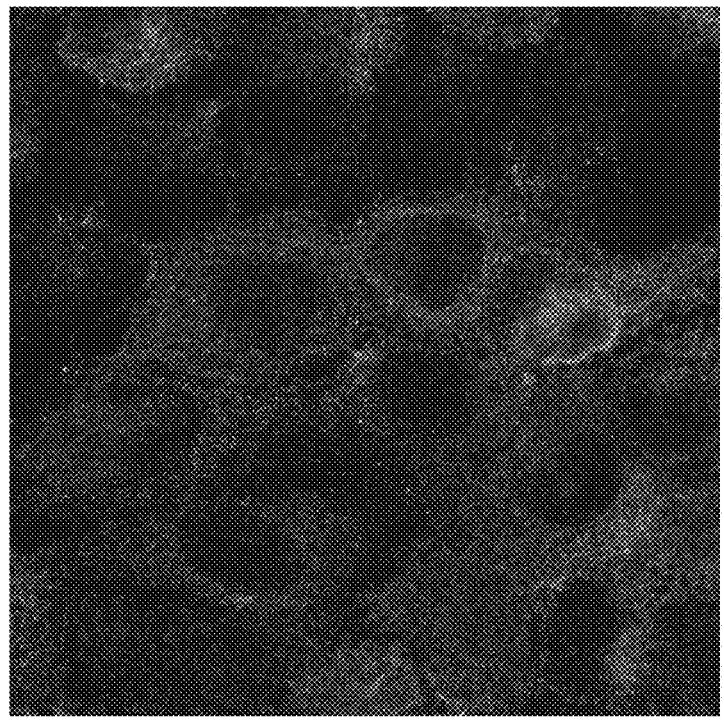

HaCat keratinocyte skin cells treated with compound 9 (10 µM) for 5 days. The fixed coverslips were then stained with Involucrin (green) and K14 (red) and imaged using a confocal microscope. The fluorescence of compound 9 is coloured in blue. Involucrin selectively stains Cellular Retinoic Acid BindingProtein (CRABP), which transports retinoids in and around the nucleus. K14 is a prototypic marker of dividing basal keratinocytes and helps in the maintenance of epidermal cell shape.

FIG. 25

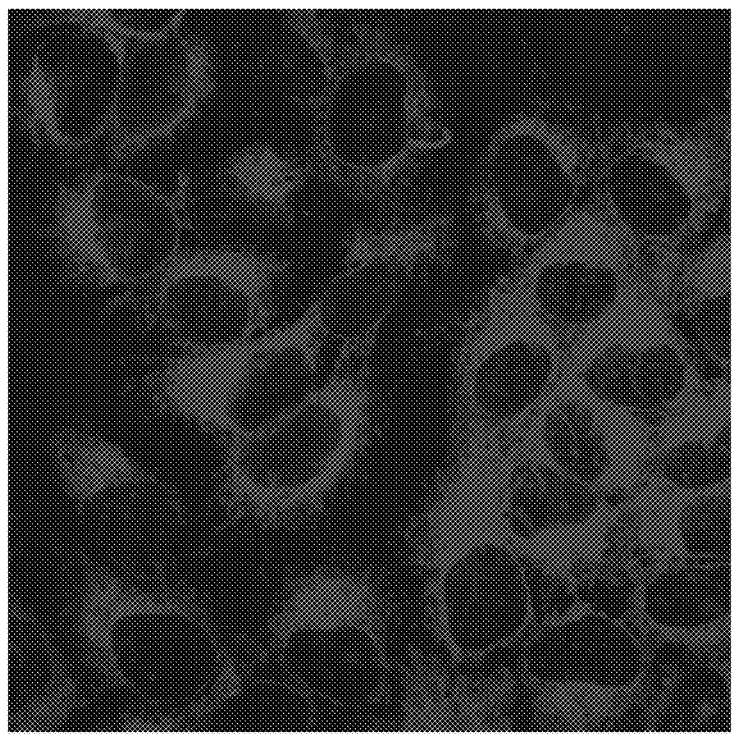

HaCat keratinocyte skin cells treated with compound 17 (10 µM) for 5 days, fixed and then imaged with a confocal microscope.

FIG. 26

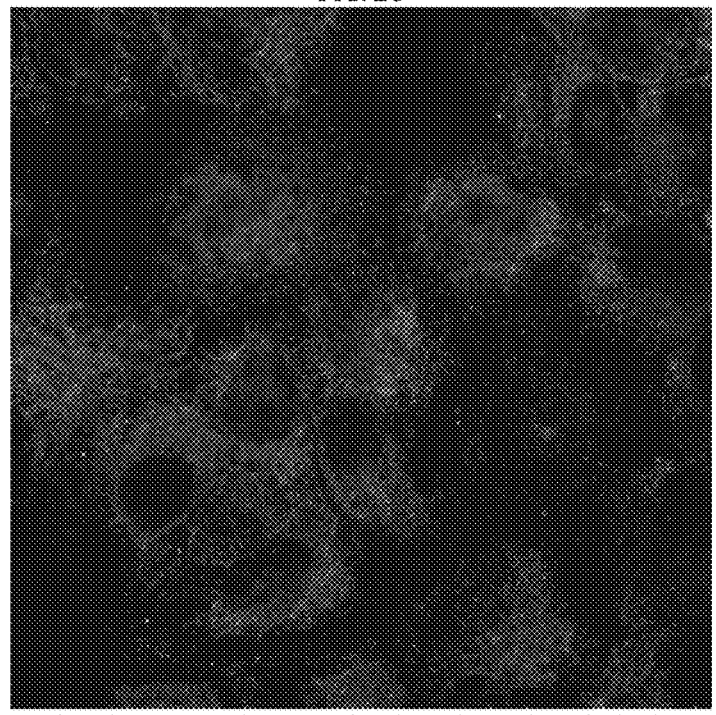

HaCat keratinocyte skin cells treated with compound 17 (10 µM) for 5 days. The fixed coverslips were then stained with Involucrin (green) and K14 (red) and imaged using a confocal microscope. The fluorescence of compound 9 is coloured in blue. Involucrin selectively stains Cellular Retinoic Acid Binding Protein (CRABP), which transports retinoids in and around the nucleus. K14 is a prototypic marker of dividing basal keratinocytes and helps in the maintenance of epidermal cell shape.

FIG. 27

Raman spectrum of compound 9. A high intensity acetylene band at 2190 cm⁻¹ is observed in the 'cellular silent region' (1800-2800 cm⁻¹).

FLUORESCENT SYNTHETIC RETINOIDS

CROSS REFERENCE TO RELATED APPLICATIONS

This is the national phase under 35 U.S.C. § 371 of International Application No. PCT/GB2015/052956, filed on Oct. 9, 2015, which claims priority to and the benefit of United Kingdom Patent Application Nos. 1417957.6, filed on Oct. 10, 2014 and 1419496.3, filed on Oct. 31, 2014, the entire disclosures of each of which are incorporated by reference herein.

FIELD OF THE INVENTION

The present invention relates to novel compounds, their use and methods of treatment related thereto.

More particularly, the present invention relates to novel fluorescent synthetic retinoid compounds and their use in the control of cell differentiation. The invention also provides a method of medical treatment using the novel compounds of the invention.

BACKGROUND TO THE INVENTION

Vitamin A (retinol) and its derivatives belong to a class of compounds known as retinoids. Retinoids are an important class of signalling molecules that are involved in controlling many important biological pathways from embryogenesis through to adult homeostasis and many aspects of stem cell development, such as, stem cell proliferation, differentiation and apoptosis.

Retinoids are structurally and/or functionally related to vitamin A; and many possess biological activity including all-trans-retinoic acid (ATRA). ATRA is the most abundant endogenous retinoid and has been widely studied for many years; ATRA isomerises under physiological and experimental conditions, with different isomers activating different receptors, thus accounting for the variety of biological effects observed with these small molecules.

Due to the ability of retinoids to control differentiation and apoptosis in both normal and tumour cells, they have the potential to act as chemopreventative and chemotherapeutic agents, although toxicity has prevented widespread use.

However, ATRA exhibits poor stability, in particular upon exposure to light. ATRA compounds isomerise and degrade upon exposure to light. To overcome this, efforts are made to store and work with ATRA in the dark, but such precautions increase the cost associated with working with ATRA, and do not entirely mitigate the problem. Furthermore, as ATRA is liable to photoisomerisation and degradation upon storage, it is difficult to predict accurately the amount of active compound administered in a single dose. Efforts have been made to overcome the problems associated with ATRA by synthesising stable retinoid compounds. It is generally believed that ATRA is susceptible to photoisomerisation due to its conjugated linker group.

International Patent application No. PCT/GB2007/003237 (WO 2008/025965) disclosed new retinoid compounds which exhibited good stability and induced cell differentiation.

One compound of particular interest was EC23®, which is/was marketed by Reinnervate:

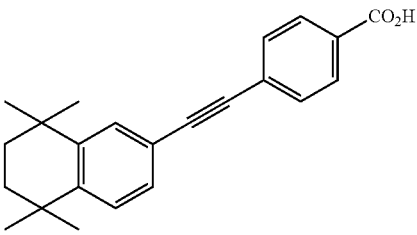 [SMILES: CC1(C)CCC(C)(C)c2cc(C#Cc3ccc(C(=O)O)cc3)ccc21]

EC23® generally exhibits good stability exposed to light, as well as exhibiting good stability upon storage. EC23® is also found to not be susceptible to metabolic degradation, and thus may have a relatively long associated half-life in the human or animal body. However, EC23® is only weakly fluorescent, and requires UV excitation, which may be damaging to biological samples.

Fluorescence imaging has rapidly become a powerful tool for investigating biological processes, particularly in living cells where cellular events may be observed in their physiological contexts. The development of single-molecule visualisation techniques has greatly enhanced the usefulness of fluorescence microscopy for such applications, enabling the tracking of proteins and small molecules in their endogenous environments.

Fluorescence is a form of luminescence in which a substance that has absorbed light or other electromagnetic radiation emits light from electronically excited states. In fluorescence, the emitted light is usually of a longer wavelength (and lower energy) than the absorbed light. This phenomenon is known as Stokes shift, and is attributed to the loss of energy, usually via vibrational relaxation to the lowest energy level of the first excited state (S1), before an absorbed photon is emitted. The quantum yield gives the efficiency of the fluorescence process: it is defined as the ratio of the number of photons emitted to the number of photons absorbed (maximum value=1, i.e. every absorbed photon results in an emitted photon). Fluorescence decay is generally exponential and the fluorescence lifetime refers to the measure of the half-life of a molecule remaining in an excited state before undergoing relaxation back to the ground state. In phosphorescence, a longer excited state lifetime is observed, followed by radiative decay (i.e. photon emission) from an excited triplet state.

Doxorubicin is a chemotherapeutic drug used in the treatment of a wide range of cancers, including leukaemia, Hodgkin's lymphoma, bladder, breast, stomach, lung, ovarian, and thyroid cancers. The amphiphilic and amphoteric nature of the molecule means that the drug is able to bind to both cell membranes and proteins.

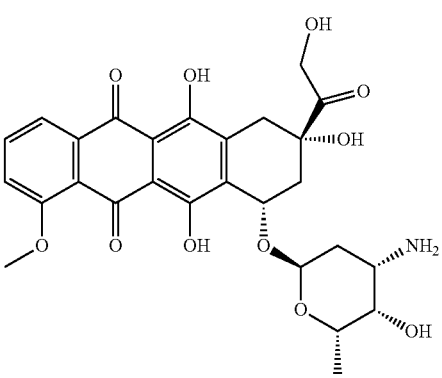

Doxorubicin

Due to the inherent fluorescence of the compound, doxorubicin has also become a popular research tool in the field of fluorescence imaging, and its distribution has accordingly been visualised in various cells and tissues. Since the fluorescence intensity of doxorubicin was found to be dependent on its concentration and microenvironment, the intracellular uptake and trafficking of the drug in ovarian carcinoma A2780 cells was able to be characterised by taking into account its interaction with cellular components such as DNA, histones, and phospholipids.

At present, doxorubicin is the only known small molecule possessing intrinsic fluorescence emission along with significant biological activity. Thus, if fluorescence could be incorporated into a small molecule modulator of stem cell development, this would in itself constitute a powerful probe, and would negate the need for the use of fluorescent dyes, proteins, and quantum dots. In particular, the use of live-cell tracking techniques would provide invaluable information concerning cellular uptake and localisation, thereby offering new insights into retinoid activity and metabolism. Furthermore, since it would no longer be necessary to attach a large fluorescent entity to the molecule of interest, the latter may be followed in the physiological context of its natural environment. In addition, it may also be advantageous to generate an inert fluorescent probe that may have useful fluorescent properties.

Therefore, for improved fluorescence imaging, there is a need for a novel fluorophore that exhibits good storage stability, and is not susceptible to metabolic degradation, thus having a relatively long associated half-life in the body. Thus, an object of the present invention is to provide a stable fluorescent retinoid.

SUMMARY TO THE INVENTION

The present invention provides fluorescent versions of EC23® type molecules by the preparation of novel molecular systems with an electron donating nitrogen to provide a highly conjugated structure.

Thus, according to a first aspect of the invention there is provided a compound of formula I:

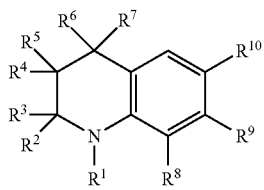

I in which
$R^1$ is hydrogen, alkyl C1-10 or acyl;
$R^2$, $R^3$, $R^4$ and $R^5$, which may be the same or different, are each hydrogen or alkyl C1-4, or together one pair of $R^2$ and $R^4$ or $R^3$ and $R^5$ represent a bond;
$R^6$ and $R^7$, which may be the same or different, are each hydrogen, alkyl C1-4 or together one pair of $R^4$ and $R^6$ or $R^5$ and $R^7$ represent a bond, or $R^6$ and $R^7$ together form a group:

=$CR^{11}R^{12}$ provided that the pair of $R^4$ and $R^6$ or $R^5$ and $R^7$ does not represent a bond if a pair from $R^2$, $R^3$, $R^4$ and $R^5$ represents a bond;
$R^8$ and $R^9$, which may be the same or different, are each hydrogen, alkyl C1-10, aryl, aralkyl, halogen, trifluoroalkyl, cyano, nitro, $-NR^aR^b$, $-OR^a$, $-C(O)R^a$, $-C(O)OR^a$, $-OC(O)R^a$, $-S(O)R^aR^b$, and $-C(O)NR^aR^b$;
$R^{11}$ and $R^{12}$, which may be the same or different, are each hydrogen or alkyl C1-10; and
$R^a$ and $R^b$, which may be the same or different, are each hydrogen or alkyl C1-10;
$R^{10}$ is a group II, III, IV, V, VI, VII, VIII, IX, X or XI:

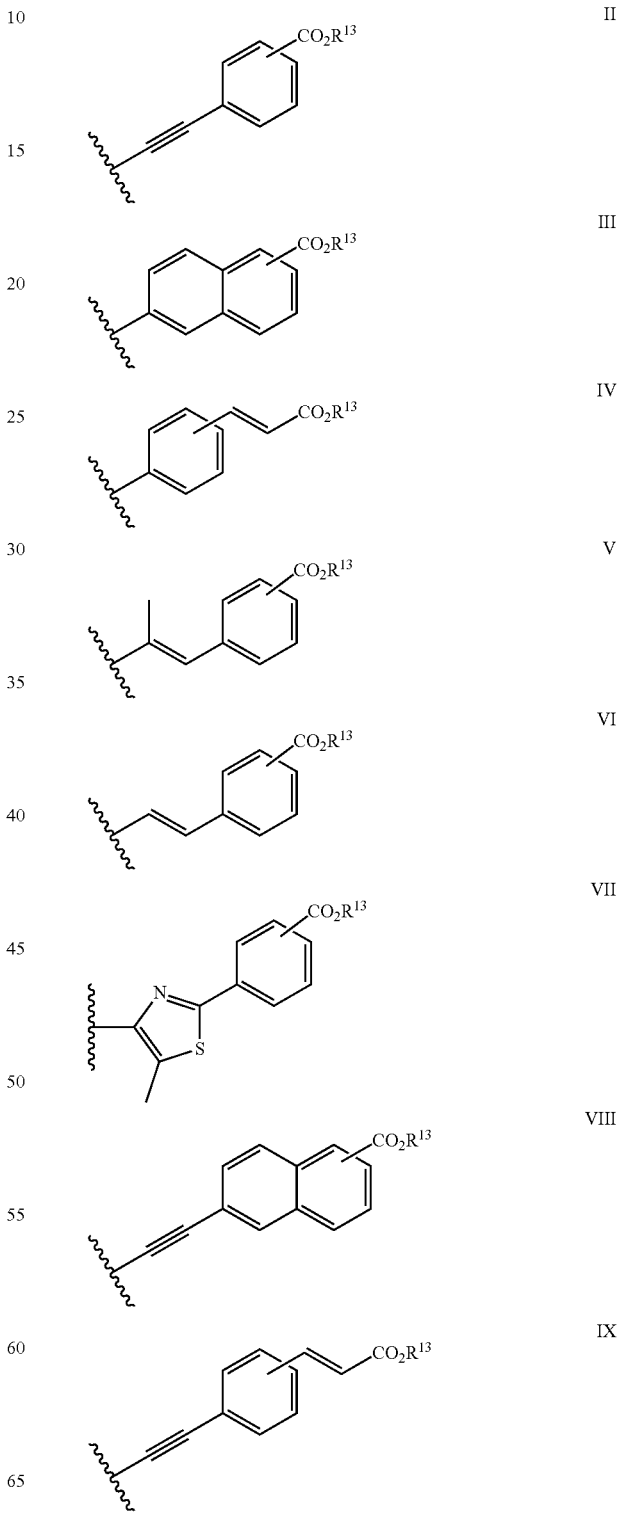

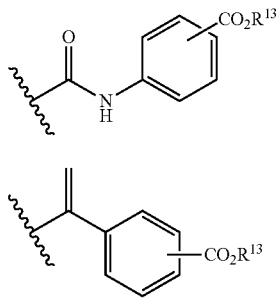

in which $R^{13}$ is hydrogen or alkyl C1-10;
and isomers thereof;
in free or in salt form.

As used herein, the term "alkyl" refers to a fully saturated, branched, unbranched or cyclic hydrocarbon moiety, i.e. primary, secondary or tertiary alkyl or, where appropriate, cycloalkyl or alkyl substituted by cycloalkyl, they may also be saturated or unsaturated alkyl groups. Where not otherwise identified, preferably the alkyl comprises 1 to 10 carbon atoms, more preferably 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein the term "aryl" refers to an aromatic monocyclic or multicyclic hydrocarbon ring system consisting only of hydrogen and carbon and containing from 6 to 19 carbon atoms, preferably 6 to 10 carbon atoms, where the ring system may be partially saturated. Aryl groups include, but are not limited to groups such as fluorenyl, phenyl, indenyl and naphthyl. Unless stated otherwise specifically in the specification, the term "aryl" or the prefix "ar-" (such as in "aralkyl") is meant to include aryl radicals optionally substituted by one or more substituents selected from the group consisting of alkyl, alkenyl, alkynyl, halo, haloalkyl, cyano, nitro, amino, amidine, aryl, aralkyl, cycloalkyl, cycloalkylalkyl, heterocyclyl, heterocyclylalkyl, heteroaryl or heteroarylalkyl. Preferred aryl groups are optionally substituted phenyl or naphthyl groups.

An aryl group may be mono-, bi-, tri-, or polycyclic, preferably mono-, bi-, or tricyclic, more preferably mono- or bicyclic.

In one aspect of the invention $R^{10}$ is a group II, III or IV as herein defined.

In one aspect of the invention $R^1$ is alkyl C1-10, preferably alkyl C1-3.

In one aspect of the invention $R^2$, $R^3$, $R^4$ and $R^5$ are each hydrogen.

In one aspect of the invention one pair of $R^2$ and $R^4$ or $R^3$ and $R^5$ represent a bond.

In one aspect of the invention $R^6$ and $R^7$ are the same or different; $R^6$ and $R^7$ may each represent alkyl C1-4, e.g. methyl.

As used herein, the term "halogen" or "halo" refers to fluoro, chloro, bromo, and iodo.

In another aspect of the invention $R^{10}$ is a group II, as herein defined.

In another aspect of the invention $R^{10}$ is a group III, as herein defined.

In another aspect of the invention $R^{10}$ is a group IV, as herein defined.

In another aspect of the invention $R^{10}$ is a group V, as herein defined.

In another aspect of the invention $R^{10}$ is a group VI, as herein defined.

In another aspect of the invention $R^{10}$ is a group VII, as herein defined.

In another aspect of the invention $R^{10}$ is a group VIII, as herein defined.

In another aspect of the invention $R^{10}$ is a group IX, as herein defined.

In another aspect of the invention $R^{10}$ is a group X, as herein defined.

In another aspect of the invention $R^{10}$ is a group XI, as herein defined.

The moiety —$CO_2R^{13}$ is preferably in the 4-position, i.e. in the para position to the ethynyl group. Preferably $R^{13}$ is hydrogen.

A specific compound of formula I which may be mentioned include those selected from the group consisting of:
4-2-[4,4-dimethyl-1-(propan-2-yl)-1,2,3,4-tetrahydroquinolin-6-yl]ethynylbenzoic acid, (9); and
6-(1,4,4-trimethyl-1,2,3,4-tetrahydroquinolin-6-yl)-naphthalene-2-carboxylic acid methyl ester (11);
3-[4-(1,4,4-trimethyl-1,2,3,4-tetrahydroquinolin-6-yl)-phenyl]-acrylic acid methyl ester (13); and
4-2-[2,4,4-trimethyl-1-(propan-2-yl)-1,4-dihydroquinolin-6-yl]ethynylbenzoic acid, (17);
and isomers thereof;
in free or in salt form.

Retinoid compounds such as ATRA are unstable upon storage. In particular, such compounds are susceptible to photoisomerisation and degradation upon exposure to light in the 300 to 400 nm region. Surprisingly, the compounds of formula I of the present invention are stable upon exposure to light and undergo far less photoisomerisation and degradation than ATRA. Generally the compounds of formula 1 have far better stability than retinoids such as ATRA, in particular the compounds of formula 1 are far less susceptible to photoisomerisation. Generally, following 3 days exposure to light having a wavelength of 300 to 400 nm, the compounds of the present invention undergo far less isomerisation and degradation than ATRA. Typically at least 60% by weight of the compounds of the present invention remain (compared to less than 40% by weight ATRA) following 3 days exposure to light of wavelength 300 to 400 nm.

Typically, the compounds of the present invention induce the differentiation of stem cells, such as human neural stem cells into neural sub-types. Generally the compounds of the present invention induce differentiation of cells to an extent commensurate to or greater than known retinoids such as ATRA.

Following exposure of a sample comprising stem cells, for instance a cell derived from the ventral mesencephalon of human foetal brain tissue, to media supplemented with the compounds of the present invention the number of differentiated cells expressing neuronal markers may be substantially increased. Typically the sample may be exposed to such media for around 7 days.

In a preferred use according to the invention there is provided the use of a compound or composition as defined herein in the differentiation of a stem cell into at least one differentiated cell type.

The stem cell may typically be a human or animal totipotent stem cell, in particular a non-human totipotent stem cell for example a totipotent cell of a mammal, for example a mouse, a rat or a rabbit.

Alternatively, the stem cell may be a pluripotent stem cell of a human or animal, preferably a human pluripotent stem cell.

In an alternative preferred embodiment of the invention said stem cell is a multipotent stem cell of a human or animal.

In a preferred embodiment of the invention said multipotent stem cell is selected from the group consisting of: haemopoietic stem cell, neural stem cell, bone stem cell, muscle stem cell, mesenchymal stem cell, epithelial stem cell (derived from organs such as the skin, gastrointestinal mucosa, kidney, bladder, mammary glands, uterus, prostate and endocrine glands such as the pituitary), ectodermal stem cell, mesodermal stem cell or endodermal stem cell (for example derived from organs such as the liver, pancreas, lung and blood vessels).

According to a further aspect of the invention there is provided a method of inducing the differentiation of a stem cell comprising the steps of:
(i) forming a preparation of stem cells in a cell culture medium suitable for maintaining said stem cells wherein said culture medium comprises a compound according to formula I; and
(ii) cultivating said stem cells in conditions that allow their differentiation into at least one differentiated cell type.

In a preferred method of the invention said stem cell is a multipotent or pluripotent stem cell. According to one embodiment the stem cell is not a totipotent stem cell. Preferably said stem cell is of human origin.

In a preferred method of the invention said differentiated cell is selected from the group consisting of a keratinocyte, a fibroblast (e.g. dermal, corneal, intestinal mucosa, oral mucosa, bladder, urethral, prostate, liver), an epithelial cell (e.g. dermal, corneal, intestinal mucosa, oral mucosa, bladder, urethral, prostate, liver), a neuronal glial cell or neural cell, a hepatocyte, a mesenchyma cell, a muscle cell (cardiomyocyte or myotube cell), a kidney cell, a blood cell (e.g. CD4+ lymphocyte, CD8+ lymphocyte), a pancreatic cell, or an endothelial cell.

Generally the medium has a concentration of 0.1 to 20 µM of the compound of the present invention; typically around 10 µM.

In a preferred method of the invention the method takes place in the presence of visible and/or UV light, temperatures not exceeding 50° C. and/or oxidative reagents for example air or DMSO. The method of the invention may take place ex vivo, in vivo or in vitro.

The compounds of the invention exhibit good stability and can be used to control cell differentiation and cell apoptosis.

Thus, according to a further aspect of the present invention there is provided the use of a compound according to formula I in the treatment or prevention of a disease or condition that would benefit from retinoid therapy.

The compounds of formula I exhibit good stability, and undergo photoisomerisation far less easily than ATRA, whilst controlling cell differentiation and apoptosis to an extent commensurate with or greater than ATRA.

According to a further aspect of the present invention there is provided a compound of formula I for use in the control of cell differentiation or apoptosis.

The disease or condition typically benefits from the control of cell differentiation or apoptosis.

Diseases or conditions that may benefit from retinoid therapy include cancer (e.g. neural neoplasms), skin disorders such as acne, skin wounds e.g. burns, UV damage, aging skin.

The compounds of the present invention may act as chemotherapeutic or chemopreventative agents due to their ability to control differentiation and apoptosis in normal and tumour cells. In particular the compounds of the present invention may be particularly well suited to the treatment or prevention of precancerous or cancerous conditions including those of the skin, oral cavity, larynx, lung, bladder, vulva, breast, digestive tract. The compounds of the present invention may be used in the treatment or prevention of basal cell carcinomas, squamous cell carcinomas, including those of the head and neck, bladder tumours. Cancers particularly suited for treatment or prevention through use of the compounds of the present invention include leukaemia, such as myelogenous leukaemia, in particular acute promyelocyte leukaemia.

It is believed that the compounds of the present invention suppress transformation of cells in vitro and inhibit carcinogenesis. It is believed that the compounds of the present invention thus exhibit suppressive effects on tumour promotion, and/or tumour initiation. When used as chemotherapeutic agents, the compounds of the present invention generally arrest or reverse carcinogenic steps, reducing or avoiding the clinical consequences of overt malignancies.

It is believed that the compounds of the present invention exhibit chemotherapeutic and/or chemopreventative properties due to their ability to modulate the growth, differentiation, and apoptosis of normal, premalignant, and malignant cells in vitro and in vivo.

According to a further aspect of the present invention there is provided the use of the compounds of the present invention in the promotion of cell proliferation, for example skin or neural cell proliferation.

According to a further aspect of the present invention there is provided the use of the compounds of the present invention in promoting tissue health and development, in particular in promoting the health and development of the skin, bone, nerves teeth, hair and/or mucous membranes of the human or animal body. The compounds of the present invention may be used in the prevention or treatment of the signs of ageing (in particular, wrinkles and age spots), skin conditions such as acne (especially severe and/or recalcitrant acne), psoriasis, stretch marks, keratosis pilaris, emphysema, baldness.

According to a further aspect of the present invention, the compounds of the present invention may be used in the treatment or prevention of diseases or conditions of the eye, or may be used to maintain or maximise vision.

According to a further aspect of the present invention, the compounds of the present invention may be used as antioxidants, in particular for use in or on the human or animal body.

The dosage of the compound of the present invention to be administered to the human or animal body is dependent on the intended use. For instance, formulations suitable for topical application generally comprise 0.025 to 1 wt % compound of the present invention, in particular, 0.025 to 0.1 wt %. For chemotherapeutic uses, a dosage of 20 to 80 mg/m²/day is usual, suitably 40 to 50 mg/m²/day, more suitably around 45 mg/m²/day.

As herein described, the compounds of the present invention are inherently fluorescent.

Therefore, according to a further aspect of the invention there is provided a probe comprising a compound of formula I as herein described.

The invention further provides a method of monitoring cell differentiation or apoptosis comprising administering an effective amount of a compound of formula I and detecting the fluorescence emitted by the compound of formula I by fluorescence medical imaging.

The invention also provides a method of monitoring cell differentiation or apoptosis by imaging the distribution of a compound of formula I by detecting the fluorescence emitted by the compound using techniques that include, but are not limited to, fluorescence lifetime mapping microscopy (FLIM).

In another aspect the invention also provides a method of monitoring cell differentiation or apoptosis by imaging the distribution of a compound of formula I by detecting the Raman scattering signal stimulated by techniques that include, but are not limited to coherent anti-Stokes Raman scattering (CARS) and stimulated Raman scattering (SRS).

The invention also provides a method of monitoring the intracellular or extracellular concentration and distribution of a compound of formula I by techniques that include, but are not limited to multivariate curve resolution (MCR) and least-squares analysis of Raman scattering signals to allow the creation of a concentration map of a compound of formula I ex vivo, in vivo or in vitro.

In addition, the invention provides a method for superimposing fluorescence emitted by a compound of formula I with a Raman scattering signal stimulated from a compound of formula I. This method for superimposing emitted fluorescence may be be useful in the method of monitoring cell differentiation or apoptosis herein described.

Compounds of formula I may also be advantageous in that the compounds may be used selectively for different cell types, i.e. that visible, fluorescence and/or Raman imaging may be used to identify cell types that are more responsive to the synthetic molecules of the invention. This may provide a cell identification method. Observing the fluorescent lifetime of the compound of the invention may provide information on the local environment and potentially on the ongoing action of the compound. Also, cells treated with the fluorescent compounds of the invention may then be treated with other molecules, for example, to "displace" the fluorescent compounds to give a measure of relative affinity, which may be useful for, inter alia, drug screening. Thus, the fluorescent compounds of the invention may be used in combination with other suitably known compounds.

According to a further aspect of the present invention there is provided a composition comprising one or more of the compounds of the present invention in combination with one or more pharmaceutically acceptable excipients.

The composition of the present invention also includes one or more pharmaceutically acceptable carriers, excipients, adjuvants or diluents. The phrase "pharmaceutically acceptable" is employed herein to refer to those compounds, materials, compositions, and/or dosage forms which are, within the scope of sound medical judgment, suitable for use in contact with the tissues of human beings or, as the case may be, an animal without excessive toxicity, irritation, allergic response, or other problem or complication, commensurate with a reasonable benefit/risk ratio.

When the composition of the invention is prepared for oral administration, the compounds described above are generally combined with a pharmaceutically acceptable carrier, diluent or excipient to form a pharmaceutical formulation, or unit dosage form.

For oral administration, the composition may be in the form of a powder, a granular formation, a solution, a suspension, an emulsion or in a natural or synthetic polymer or resin for ingestion of the active ingredients from a chewing gum. The composition may also be presented as a bolus, electuary or paste. Orally administered compositions of the invention can also be formulated for sustained release, e.g. the compounds described above can be coated, microencapsulated, or otherwise placed within a sustained delivery device. The total active ingredients in such formulations comprise from 0.1 to 99.9% by weight of the formulation.

Thus, one or more suitable unit dosage forms comprising the compounds of the invention can be administered by a variety of routes including oral, parenteral (including subcutaneous, intravenous, intramuscular and intraperitoneal), rectal, dermal, transdermal, intrathoracic, intrapulmonary, mucosal, intraocular and intranasal (respiratory) routes. The composition may also be formulated in a lipid formulation or for sustained release, for example, using microencapsulation. The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

Pharmaceutical formulations comprising the compounds of the invention can be prepared by procedures known in the art using well-known and readily available ingredients. For example, the compound can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives.

Binding agents can also be included such as carboxymethyl cellulose, hydroxymethylcellulose, hydroxypropyl methylcellulose and other cellulose derivatives, alginates, gelatine, and polyvinylpyrrolidone. Moisturising agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing the compounds of the invention can include buffering agents such as calcium carbonate, magnesium oxide and magnesium carbonate. Suitable buffering agents may also include acetic acid in a salt, citric acid in a salt, boric acid in a salt and phosphoric acid in a salt. Caplets and tablets can also include inactive ingredients such as cellulose, pregelatinised starch, silicon dioxide, hydroxyl propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatine capsules containing at least one compound of the invention can contain inactive ingredients such as gelatine, microcrystalline cellulose, sodium lauryl sulphate, starch, talc, and titanium dioxide, and the like, as well as liquid vehicles such as polyethylene glycols (PEGs) and vegetable oil. Moreover, enteric-coated caplets or tablets containing one or more compounds of the invention are designed to resist disintegration in the stomach and dissolve in the more neutral to alkaline environment of the duodenum.

The therapeutic compounds of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic compounds of the invention can also take the form of an aqueous or anhydrous solution or dispersion, or alternatively the form of an emulsion or suspension or salve.

Thus, the therapeutic compounds may be formulated for parenteral administration (e.g. by injection, for example, bolus injection or continuous infusion) and may be presented in unit dose form in ampules, pre-filled syringes, small volume infusion containers or in multi-dose containers. As noted above, preservatives can be added to help maintain the shelve life of the dosage form. The active compound(s) and other ingredients may form suspensions, solutions, or emulsions in oily or aqueous vehicles, and may contain formulatory agents such as suspending, stabilizing and/or dispersing agents. Alternatively, the active compound(s) and other ingredients may be in powder form, obtained by aseptic isolation of sterile solid or by lyophilisation from solution for constitution with a suitable vehicle, e.g., sterile, pyrogen-free water before use.

It is possible to add, if necessary, an adjuvant chosen from antioxidants, surfactants, other preservatives, film-forming, keratolytic or comedolytic agents, perfumes, flavourings and colourings. Antioxidants such as t-butylhydroquinone, butylated hydroxyanisole, butylated hydroxytoluene and α-tocopherol and its derivatives can be added.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, acetic acid, ethanol, isopropyl alcohol, dimethyl sulphoxide, glycol ethers such as the products sold under the name "Dowanol", polyglycols and polyethylene glycols, C1-C4 alkyl esters of short-chain acids, ethyl or isopropyl lactate, fatty acid triglycerides such as the products marketed under the name "Miglyol", isopropyl myristate, animal, mineral and vegetable oils and polysiloxanes.

Preferably, the composition is in the form of a solvent or diluent comprising one or more of the compounds as described above. Solvents or diluents may include acid solutions, dimethylsulphone, N-(2-mercaptopropionyl) glycine, 2-n-nonyl-], 3-dioxolane and ethyl alcohol. Preferably the solvent/diluent is an acidic solvent, for example, acetic acid, citric acid, boric acid, lactic acid, propionic acid, phosphoric acid, benzoic acid, butyric acid, malic acid, malonic acid, oxalic acid, succinic acid or tartaric acid.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0.

The solvent may comprise an acetic acid solution. The solvent, for example acetic acid solution, may be present in the composition at a concentration of less than 1%, 0.5%, 0.25%, 0.1%, 0.05% or 0.01% w/w acid, for example acetic acid.

The composition of the present invention may comprise one or more additional therapeutic agents. For instance, where the composition of the present invention is useful in the treatment or prevention of cancer, one or more additional chemotherapeutic and or chemopreventative agents may be included. Where the composition is useful in skincare one or more additional skincare agent may be used such as one or more moisturising or antibacterial agent.

Additionally, the compounds of the present invention are well suited to formulation as sustained release dosage forms and the like. The formulations can be so constituted that they release the active compound, for example, in a particular part of the intestinal or respiratory tract, possibly over a period of time. Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g. stents, catheters, peritoneal dialysis tubing, draining devices and the like.

For topical administration, the active agents may be formulated as is known in the art for direct application to a target area. Forms chiefly conditioned for topical application take the form, for example, of creams, milks, gels, powders, dispersion or microemulsions, lotions thickened to a greater or lesser extent, impregnated pads, ointments or sticks, aerosol formulations (e.g. sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the therapeutic compounds of the invention can be delivered via patches or bandages for dermal administration. Alternatively, the therapeutic compounds can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 μm.

Pharmaceutical formulations for topical administration may comprise, for example, a physiologically acceptable buffered saline solution containing between about 0.001 mg/ml and about 100 mg/ml, for example between 0.1 mg/ml and 10 mg/ml, of one or more of the compounds of the present invention specific for the indication or disease to be treated.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents. The active compounds can also be delivered via iontophoresis. The percentage by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the therapeutic compounds in an aqueous or non-aqueous base also comprising one or more dispersing agents, solubilizing agents or suspending agents. Liquid sprays can be pumped, or are conveniently delivered from pressurized packs. Drops can be delivered via a simple eye dropper-capped bottle, via a plastic bottle adapted to deliver liquid contents drop-wise, or via a specially shaped closure.

The therapeutic compound may further be formulated for topical administration in the mouth or throat. For example, the active ingredients may be formulated as a lozenge further comprising a flavoured base, usually sucrose and acacia or tragacanth; pastilles comprising the composition in an inert base such as gelatine and glycerine or sucrose and acacia; and mouthwashes comprising the composition of the present invention in a suitable liquid carrier.

The compounds of the invention can also be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of a specific infection, indication or disease. Any statistically significant attenuation of one or more symptoms of an infection, indication or disease that has been treated pursuant to the method of the present invention is considered to be a treatment of such infection, indication or disease within the scope of the invention.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g. gelatine or blister packs from which the powder may be administered with the aid of an inhalator, insufflator, or a metered-dose inhaler.

The compounds of the present invention can also be administered in an aqueous solution when administered in an aerosol or inhaled form. Thus, other aerosol pharmaceutical formulations may comprise, for example, a physiologically acceptable buffered saline solution containing between about 0.001 mg/ml and about 100 mg/ml of one or more of the compounds of the present invention specific for the indication or disease to be treated. Dry aerosol in the form of finely divided solid particles of the compounds described above that are not dissolved or suspended in a liquid are also useful in the practice of the present invention. Compounds of the present invention may be formulated as dusting powders and comprise finely divided particles having an average particle size of between about 1 and 5 µm, alternatively between 2 and 3 µm. Finely divided particles may be prepared by pulverization and screen filtration using techniques well-known in the art. The particles may be administered by inhaling a predetermined quantity of the finely divided material, which can be in the form of a powder. It will be appreciated that the unit content of active ingredient or ingredients contained in an individual aerosol dose of each dosage form need not in itself constitute an effective amount for treating the particular infection, indication or disease since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the therapeutic compounds of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Furthermore, the active ingredients may also be used in combination with other therapeutic agents, for example one or more of pain relievers, anti-inflammatory agents, antihistamines, bronchodilators, chemoprotective agents, chemotherapeutic agents, antibacterial agents and the like.

According to an additional aspect of the invention there is provided a process for the manufacture of a compound of formula I as herein described which comprises reacting a compound of formula XII;

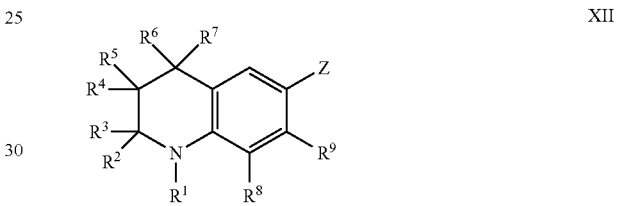

in which $R^1$, $R^2$, $R^3$, $R^4$, $R^5$, $R^6$, $R^7$, $R^8$ and $R^9$ are each as herein defined; and Z is a leaving group, for example, halogen, pseudohalogen, boronic acid or boronate ester;

with a compound of formula XIII;

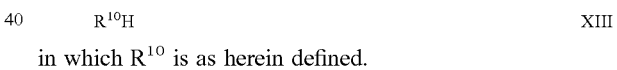

in which $R^{10}$ is as herein defined.

Alternatively, a process for the manufacture of a compound of formula I as herein described may comprise reacting a compound of formula XV;

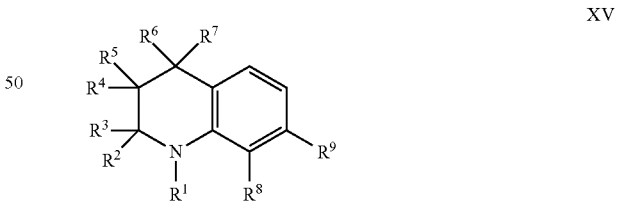

in which $R^1$, $R^2$, $R^3$, $R^4$, $R^5$, $R^6$, $R^7$, $R^8$ and $R^9$ are each as herein defined; with a compound of formula XIV:

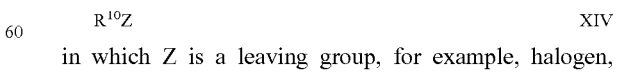

in which Z is a leaving group, for example, halogen, pseudohalogen, boronic acid or boronate ester.

Compounds of formula I in which $R^{10}$ is hydrogen may be prepared by dealkylation of a compound of formula I in which $R^{10}$ is alkyl as herein described.

Compounds of formula I, XII, XIII and XIV may be prepared using methods known to the person skilled in the art or by methods described herein. Examples of such preparations are shown schematically:
Scheme I
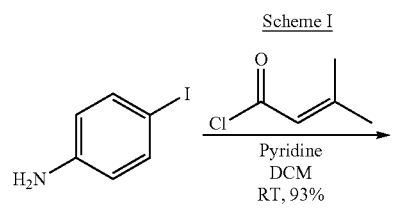
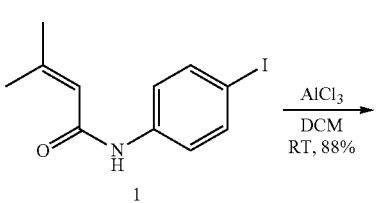
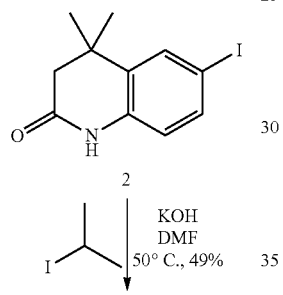
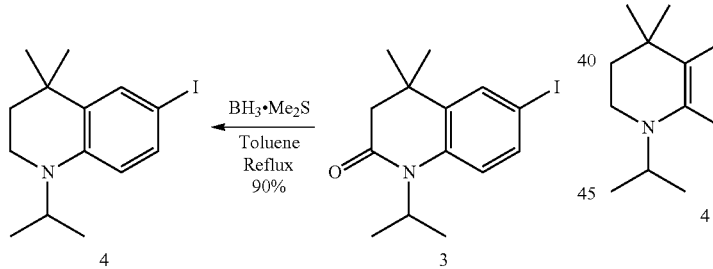
Scheme II
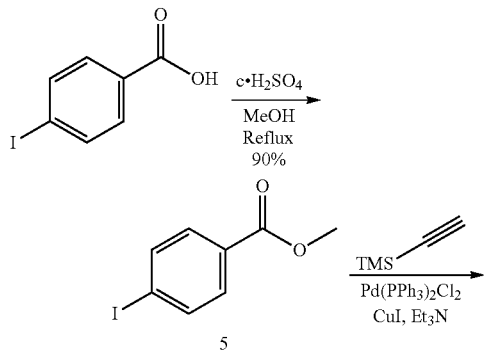
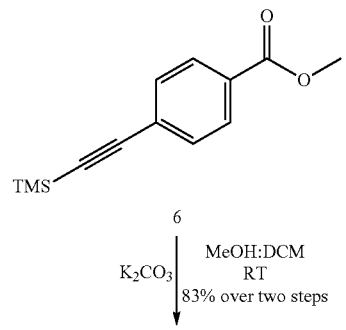
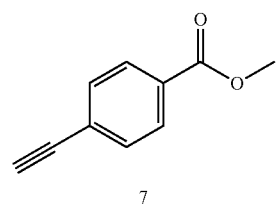
Scheme III
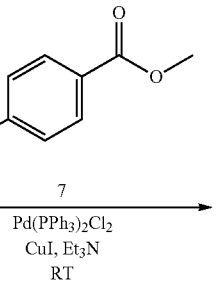
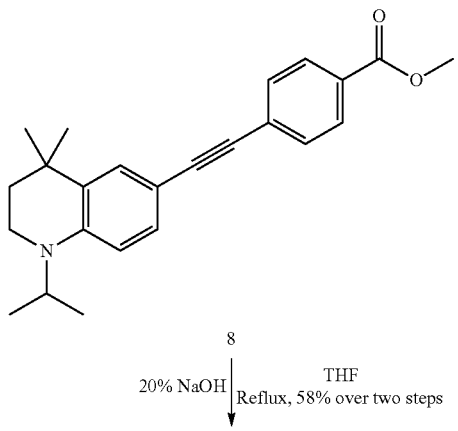

17

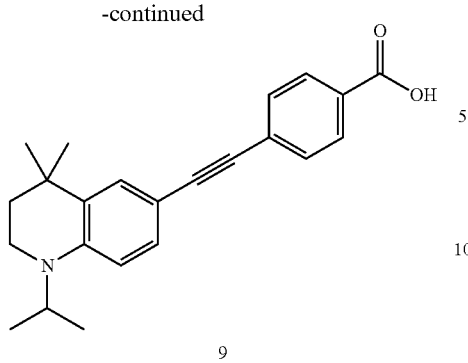

9

Naphthalene esters (compound 11) and acrylic acid ester compounds (compound 13) may be prepared by coupling the appropriate arylboronate with the appropriate naphthalene moiety, e.g. 6-bromo-naphthalene-2-carboxylic acid methyl ester; and the appropriate cinnamic acid ester, e.g. 3-bromo-methylcinnamate respectively.

Scheme IV

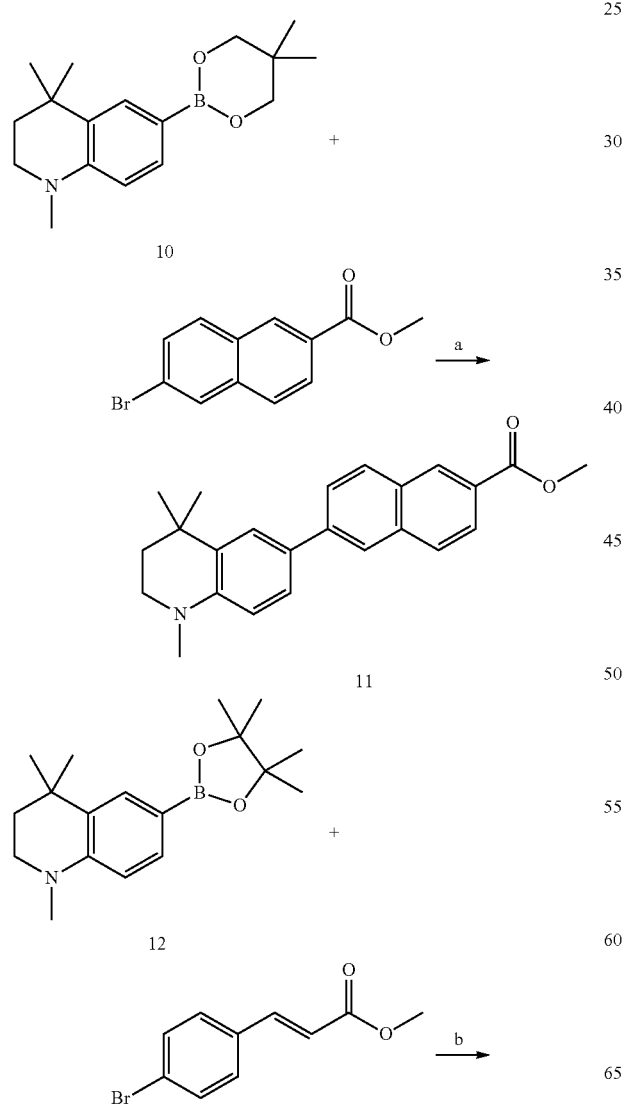

18

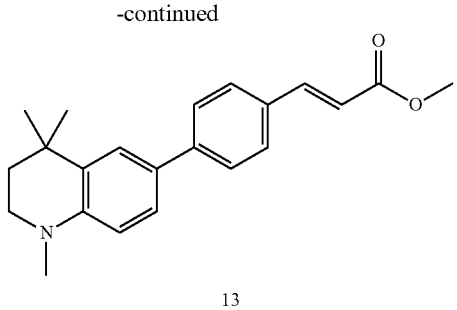

13 a) 2 mol % Pd(dppf)Cl$_2$, 2 equiv. K$_3$PO$_4$, DMF/H$_2$O 80° C., 18 h, 93%
b) 2 mol % Pd(dppf)Cl$_2$, 2 equiv. K$_3$PO$_4$, iPrOH/H$_2$O 80° C., 18 h, 66%

The aryl boronates may be prepared by the Pd-catalysed borylation of iodide 14 with either B$_2$pin$_2$ or B$_2$neop$_2$ in the presence of 5 mol % Pd(dppf)Cl$_2$ catalyst and 2 equivalents of KOAc base in DMSO gave the arylboronates 12 and 10 in good yields, giving an effective method for the selective functionalisation of the para position, relative to the electron-donating amino group.

Scheme V

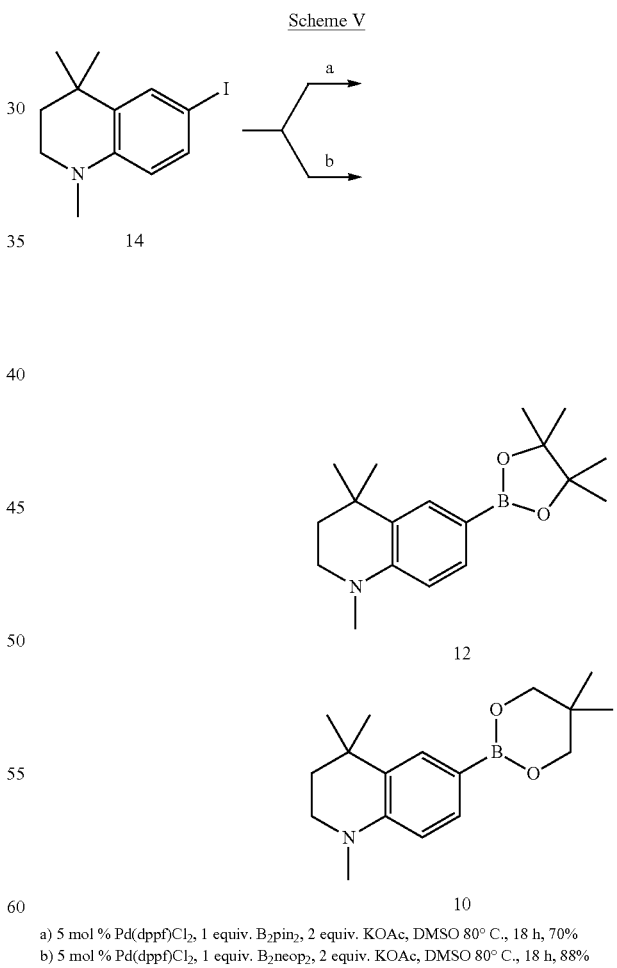

a) 5 mol % Pd(dppf)Cl$_2$, 1 equiv. B$_2$pin$_2$, 2 equiv. KOAc, DMSO 80° C., 18 h, 70%
b) 5 mol % Pd(dppf)Cl$_2$, 1 equiv. B$_2$neop$_2$, 2 equiv. KOAc, DMSO 80° C., 18 h, 88%

Dihydroquinoline-derived compounds such as 17 can be prepared by an initial Grignard methylation of amide 3, followed by Sonogashira coupling and saponification.

Scheme VI

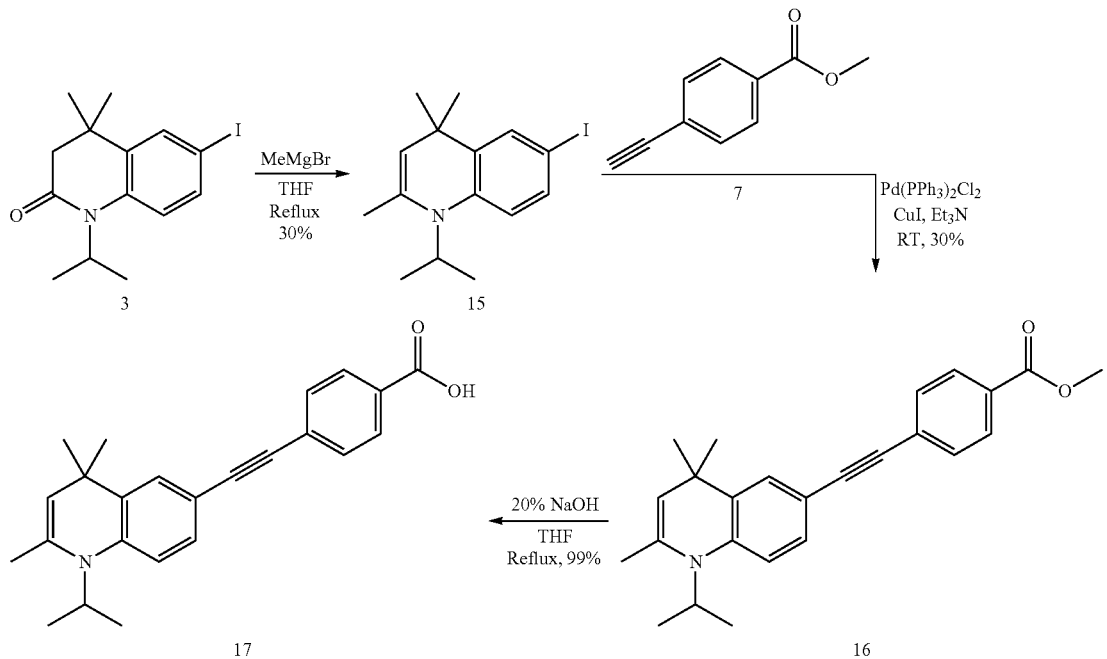

The present invention will now be described by way of example only with reference to the accompanying figures in which:

FIG. 9 illustrates compound 9 of Example 3 activity in stem cells compared to ATRA, EC23® and DMSO-Nestin staining;

FIG. 13 illustrates compound 9 of Example 3 activity in stem cells compared to ATRA, EC23® and DMSO-Sox 2 staining;

FIG. 14 illustrates flow cytometry evaluation of compound 9 of Example 3 compared to ATRA, EC23® and DMSO, the expression of stem cell marker SSEA-3 is measured;

FIG. 15 illustrates flow cytometry evaluation of compound 9 of Example 3 compared to ATRA, EC23® and DMSO, the expression of stem cell marker TRA160 is measured;

FIG. 16 illustrates flow cytometry evaluation of compound 9 of Example 3 compared to ATRA, EC23® and DMSO, the expression of stem cell marker A2B5 is measured;

FIG. 17 illustrates phase contrast images of cell populations treated with compound 9 of Example 3, ATRA, EC23® and DMSO;

FIG. 18 illustrates MTT cell viability analysis of compound 9 of Example 3 with comparison to ATRA, EC23® and DMSO at a treatment concentration of 1 μM;

FIG. 19 illustrates MTT cell viability analysis of compound 9 of Example 3 with comparison to ATRA, EC23® and DMSO at a treatment concentration of 10 μM;

Figure 22:
Figure 23:
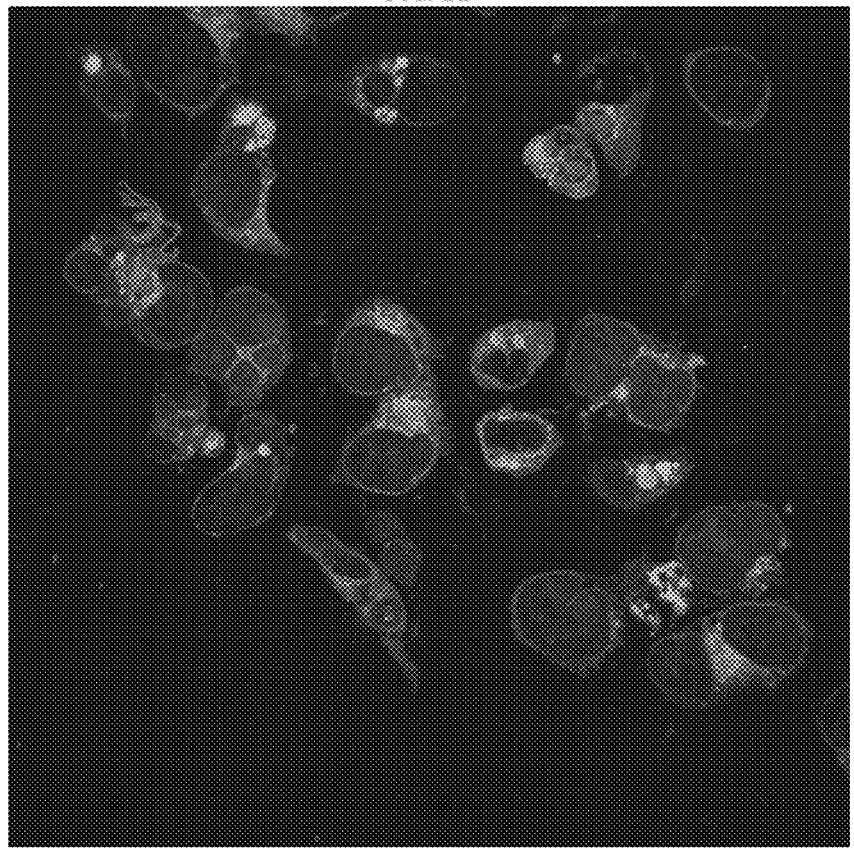
Figure 28:
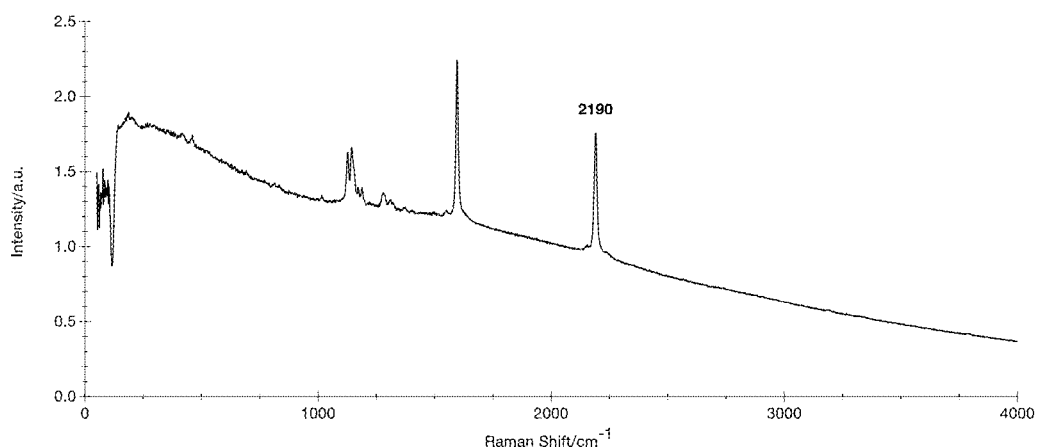

FIG. 22 Fibroblast cells treated with compound 9 of Example 3 (10 μM), and imaged using a confocal microscope after 24 hours;

FIG. 23 illustrates TERA-2 stem cells treated with compound 9 of Example 3 (10 μM) for 7 days, fixed with 4% paraformaldehyde, and imaged using a confocal microscope;

FIG. 24 illustrates HaCat keratinocyte skin cells treated with compound 9 of Example 3 (10 μM) for 5 days;

FIG. 25 illustrates HaCat keratinocyte skin cells treated with compound 9 of Example 3 (10 μM) for 5 days, and stained with Involucrin and K14;

FIG. 26 illustrates HaCat keratinocyte skin cells treated with compound 17 of Example 6 (10 μM) for 5 days;

FIG. 27 illustrates HaCat keratinocyte skin cells treated with compound 17 of Example 6 (10 μM) for 5 days, and stained with Involucrin and K14; and FIG. 28 illustrates the Raman spectrum of compound 9 of Example 3. A high intensity acetylene band is observed at 2190 cm$^{-1}$, this lies in the cellular silent region (1800-2800 cm$^{-1}$), wherein signals of biological origin, such as amide bonds, are not observed.

In the figures, any reference to DC271 is a reference to compound 9 of Example 3.

The following abbreviations are used in the Examples and other parts of the description:
ATRA: All Trans-Retinoic Acid
B$_2$pin$_2$: bis(pinacolato)diboron
DCM: dichloromethane
DMF: N,N-dimethylformamide
DMSO: dimethylsulfoxide
dppf: 1,1'-ferrocenediyl-bis(diphenylphosphine)
EDTA: ethylenediaminetetraacetic acid
EtOAc: ethyl acetate
GCMS: gas chromatography-mass spectrometry
h: hour(s)
KOAc: potassium acetate
RT: room temperature
THF: tetrahydrofuran

GENERAL EXPERIMENTAL

Reagents were purchased from Sigma-Aldrich, Acros Organics, Alfa-Aesar and Fluorochem and used without further purification unless otherwise stated. Solvents were used as supplied, and dried before use with appropriate drying agents if stated. Reactions were monitored in situ by TLC, or NMR spectroscopy. Thin layer chromatography (TLC) was conducted using Merck Millipore silica gel 60G F254 25 glassplates with visualisation by UV lamp. Flash column chromatography was performed using SiO$_2$ from Sigma-Aldrich (230-400 mesh, 40-63 am, 60 Å) and monitored using TLC. NMR spectra were recorded on Varian VNMRS-700, Varian VNMRS-600, Bruker Avance-400 or Varian Mercury-400 spectrometers operating at ambient probe temperature unless otherwise stated. NMR spectra were recorded in CDCl$_3$ or DMSO-d$_6$ purchased from Goss Scientific. NMR peaks are reported as singlet (s), doublet (d), triplet (t), quartet (q), broad (br), heptet (hept), combinations thereof, or as a multiplet (m). ES-MS was performed by the Durham University departmental service using a TQD (Waters UK) mass spectrometer and Acquity UPLC (Waters Ltd, UK), and accurate mass measurements were obtained using a QTOF Premier mass spectrometer and an Acquity UPLC (Waters Ltd, UK). GCMS was performed by the Durham University departmental service using a Shimadzu QP2010-Ultra. IR spectra were recorded on a Perkin Elmer FT-IR spectrometer. Melting points were obtained using a Gallenkamp melting point apparatus. Elemental analyses were obtained by the Durham University departmental service using an Exeter Analytical CE-440 analyzer.

Synthetic Procedures

Example 1

6-Iodo-4,4-dimethyl-1-(propan-2-yl)-1,2,3,4-tetrahydroquinoline (4)

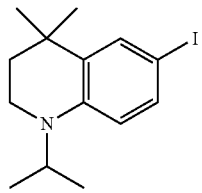 [SMILES: CC(C)N1CCC(C)(C)c2cc(I)ccc21]

1(a) N-(4-iodophenyl)-3-methylbut-2-enamide, (1)

To a solution of 4-iodoaniline, (25.0 g, 114.0 mmol) in DCM (400 mL) was added 3,3-dimethylacroloyl chloride (13.36 mL, 120.0 mmol) and the resultant white suspension was stirred for 0.5 h, after which pyridine (9.70 mL, 120 mmol) was added and the solution stirred at RT for 16 h. The solution was quenched with H$_2$O, diluted with DCM, washed with sat. NH$_4$Cl, H$_2$O and brine, dried (MgSO$_4$) and evaporated to give a crude light brown solid (33 g). This was recrystallised from EtOH to give 1 as a white crystalline solid (31.8 g, 93%): $^1$H NMR (700 MHz, CDCl$_3$) δ 1.91 (s, 3H), 2.22 (s, 3H), 5.68 (s, 1H), 7.01 (s, 1H), 7.33 (m, 2H), 7.60 (d, J=8.8 Hz, 2H); $^{13}$C NMR (101 MHz, CDCl$_3$) δ 20.2, 27.7, 87.2, 118.5, 121.8, 138.0, 138.2, 154.5, 165.2; IR (neat) $v_{max}$/cm$^{-1}$ 3294m, 3094, 2964w, 2890w, 1666m, 1586m, 1430m, 821s, 650m; MS (ES): m/z=302.0 [M+H]$^+$; HRMS (ES) calcd. for C$_{11}$H$_{13}$NOI [M+H]$^+$: 302.0042. found: 302.0050. Found: C, 43.87; H, 4.02; N 4.64. Calc. for C$_{11}$H$_{12}$NOI: C, 43.88; H, 4.02; N 4.65%; m.p.=136-138° C.

1(b) 6-Iodo-4,4-dimethyl-1,2,3,4-tetrahydroquinolin-2-one, (2)

AlCl$_3$ (7.66 g, 57.5 mmol) was added to anhydrous DCM (150 mL) and the resultant slurry stirred for 0.5 h. To this was added 1 (11.5 g, 38.3 mmol) and the solution stirred vigorously for 2.5 h at RT. The reaction was quenched slowly with H$_2$O, diluted with DCM, washed with 5% NaOH until the solution turned off-white, then further washed with H$_2$O and brine, dried (MgSO$_4$) and evaporated to give a crude yellow solid. This was recrystallised from EtOH to give 2 as a white crystalline solid (10.2 g, 88%): $^1$H NMR (700 MHz, CDCl$_3$) δ 1.32 (s, 6H), 2.47 (s, 2H), 6.62 (d, J=8.3 Hz, 1H), 7.47 (dd, J=8.3, 1.9 Hz, 1H), 7.56 (d, J=1.8 Hz, 1H), 9.20 (s, 1H); $^{13}$C NMR (176 MHz, CDCl$_3$) δ 27.7, 34.2, 45.2, 86.8, 118.1, 133.7, 135.1, 135.9, 136.6, 171.3; IR (neat) $v_{max}$/cm$^{-1}$ 3164m, 3102, 3040w, 2953m, 1671s, 1596m, 1484m, 817s; MS (ES): m/z=302.0 [M+H]$^+$; HRMS (ES) calcd. for C$_{11}$H$_{13}$NOI [M+H]$^+$: 302.0042. found: 302.0042. Found: C, 43.91; H, 4.02; N 4.63. Calc. for C$_{11}$H$_{12}$INO: C, 43.87; H, 4.02; N 4.65%; m.p.=199-202° C.

1(c) 6-Iodo-4,4-dimethyl-1-(propan-2-yl)-1,2,3,4-tetrahydroquinolin-2-one, (3)

To a solution of 2 (7.05 g, 23.4 mmol) in anhydrous DMF (200 mL) was added crushed KOH (4.08 g, 70.2 mmol) and the resultant slurry stirred for 1 h at 50° C. To this was added 2-iodopropane (7.00 mL, 70.2 mmol) and the solution stirred at 50° C. for 40 h. The reaction was quenched with H$_2$O, diluted with EtOAc, washed with sat. NH$_4$Cl, H$_2$O and brine, dried (MgSO$_4$) and evaporated to give a crude clear oil (7.2 g). This was purified by SiO$_2$ chromatography (hexane:EtOAc, 9:1, with 1% Et$_3$N, as eluent) to give 3 as a colourless oil (3.93 g, 49%): $^1$H NMR (700 MHz, CDCl$_3$) δ 1.25 (s, 6H), 1.49 (s, 3H), 1.50 (s, 3H), 2.38 (s, 2H), 4.66 (hept, J=7.0 Hz, 1H), 6.87 (d, J=8.6 Hz, 1H), 7.50 (dd, J=8.6, 2.1 Hz, 1H), 7.52 (d, J=2.1 Hz, 1H); $^{13}$C NMR (176 MHz, CDCl$_3$) δ 20.3, 26.8, 33.1, 47.2, 48.8, 86.9, 118.9, 133.4, 135.7, 138.9, 139.1, 169.5; IR (neat) ν$_{max}$/cm$^{-1}$ 2961m, 2934w, 2870w, 1667s, 1582m, 1482m, 809s; MS (ES): m/z=344.0 [M+H]$^+$; HRMS (ES) calcd. for C$_{11}$H$_{13}$NOI [M+H]$^+$: 344.0511. found: 344.0512.

1(d) 6-Iodo-4,4-dimethyl-1-(propan-2-yl)-1,2,3,4-tetrahydroquinoline, (4)

To a solution of 3 (1.25 g, 3.63 mmol) in anhydrous toluene (15 mL) at 0° C. was added borane dimethyl sulfide complex (2.0 M in THF, 1.91 mL, 3.81 mmol) dropwise and the resultant solution stirred at reflux for 16 h. The solution was cooled to RT, and 10% aq. Na$_2$CO$_3$ (25 ml) was added and the solution stirred for 0.5 h, diluted with EtOAc, washed with H$_2$O and brine, dried (MgSO$_4$) and evaporated to give a crude colourless oil (1.12 g). This was purified by SiO$_2$ chromatography (hexane:EtOAc, 9:1, with 1% Et$_3$N, as eluent) to give 4 as a colourless oil (1.08 g, 90%): $^1$H NMR (700 MHz, CDCl$_3$) δ 1.19 (s, 3H), 1.19 (s, 3H), 1.24 (s, 6H), 1.65-1.67 (m, 2H), 3.14-3.17 (m, 2H), 4.06 (hept, J=6.6 Hz, 1H), 6.46 (d, J=8.8 Hz, 1H), 7.28 (dd, J=8.9, 2.1 Hz, 1H), 7.39 (d, J=2.2 Hz, 1H); $^{13}$C NMR (176 MHz, CDCl$_3$) δ 18.9, 30.3, 32.4, 36.6, 36.8, 47.3, 76.1, 113.4, 134.5, 134.8, 135.6, 144.0; IR (neat) ν$_{max}$/cm$^{-1}$ 2957m, 2927w, 2863w, 1580m, 1489m, 792s, 684w; MS (ES): m/z=330.1 [M+H]$^+$; HRMS (ES) calcd. for C$_{11}$H$_{13}$NOI [M+H]$^+$: 330.0719. found: 330.0717.

Example 2

Methyl 4-ethynylbenzoate (7)

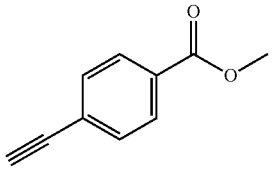

2(a) Methyl 4-iodobenzoate (5)

4-Iodobenzoic acid (25 g, 100.8 mmol) was suspended in MeOH (250 mL), and conc. H$_2$SO$_4$ (5 mL) was added and the resultant solution was stirred at reflux overnight. The clear solution was then cooled slowly to RT, and then to 0° C. The resultant solid was filtered, washed with cold MeOH and dried to give 5 as a colourless crystalline solid (23.7 g, 90%): $^1$H NMR (600 MHz, CDCl$_3$) δ 3.90 (s, 3H), 7.73 (d, J=8.6 Hz, 2H), 7.79 (d, J=8.6 Hz, 2H); $^{13}$C NMR (176 MHz, CDCl$_3$) δ 52.5, 100.9, 129.8, 131.2, 137.9, 166.7; IR (neat) ν$_{max}$/cm$^{-1}$ 3040w, 2996w, 2946w, 1709s, 1596m, 1436m, 1269s, 1114s, 843s, 683m; MS (GC): m/z=261.9 [M]$^+$. Found: C, 36.54; H, 2.71. Calc. for C8H7IO2: C, 36.67; H, 2.69%.

2(b) Methyl 4-((trimethylsilyl)ethynyl)benzoate (6)

An oven-dried 500 mL Schlenk flask was evacuated under reduced pressure and refilled with Ar, before Pd(PPh$_3$)$_2$Cl$_2$ (1.18 g, 1.68 mmol), CuI (1.68 g, 1.68 mmol) and 5 (22.0 g, 83.98 mmol) were added and the flask sealed with a septum. Triethylamine (200 mL) and trimethylsilylacetylene (13.94 mL, 100.8 mmol) were added and the flask evacuated/filled with Ar again (3×). The mixture was stirred at RT overnight. The solution was diluted with hexane, passed through Celite/SiO$_2$ under vacuum, and evaporated to give 6 as an off-white solid (19.8 g). This was carried to the next step without purification: MS (GC): m/z=232.1 [M]$^+$. Found: C, 66.90; H, 6.88. Calc. for C13H16O2Si: C, 67.2; H, 6.94%.

2(c) Methyl 4-ethynylbenzoate (7)

To a MeOH:DCM solution (2:1, 300 mL) was added 6 (18.5 g, 79.5 mmol) and K$_2$CO$_3$ (22.0 g, 159 mmol). The mixture was stirred under Ar for 6 h. The solution was then evaporated to ⅓ volume, diluted with hexane, passed through Celite and evaporated to give a light brown solid, which was purified by sublimation under reduced pressure to give 7 as a white solid (11.1 g, 83% over two steps): $^1$H NMR (600 MHz, CDCl$_3$) δ 3.23 (s, 1H), 3.91 (s, 3H), 7.54 (d, J=8.4 Hz, 2H,), 7.98 (d, J=8.6 Hz, 2H); $^{13}$C NMR (176 MHz, CDCl$_3$) δ 52.5, 80.2, 83.0, 126.9, 129.6, 130.3, 132.3, 166.6; IR (neat) ν$_{max}$/cm$^{-1}$ 3035w, 3006w, 2950w, 2103w, 1699s, 1605m, 1433m, 1277s, 1107s, 859s; MS (GC): m/z=160.1 [M]$^+$. Found: C, 74.62; H, 5.01. Calc. for C10H8O2: C, 74.99; H, 5.03%.

Example 3

4-2-[4,4-Dimethyl-1-(propan-2-yl)-1,2,3,4-tetrahydroquinolin-6-yl]ethynylbenzoic acid (9)

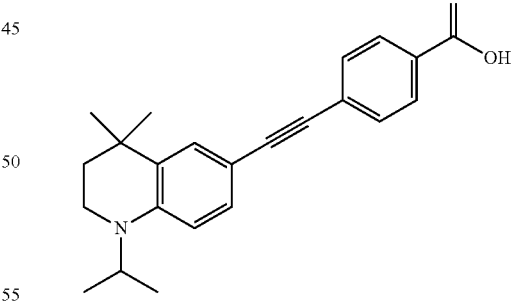

3(a) 4-2-[4,4-Dimethyl-1-(propan-2-yl)-1,2,3,4-tetrahydroquinolin-6-yl]ethynylbenzoate, (8)

An oven-dried Schlenk flask was evacuated under reduced pressure and refilled with Ar, before Pd(PPh$_3$)$_2$Cl$_2$ (0.0744 g, 0.106 mmol), CuI (0.0202 g, 0.106 mmol) and 7 (0.219 g, 1.37 mmol) were added and the flask sealed with a septum. A solution of 4 (0.349 g, 1.06 mmol) in triethylamine (6 mL) was added and the flask evacuated/filled with Ar again (3×). The mixture was stirred at RT for 72 h. The mixture was diluted with Et$_2$O, passed through Celite/SiO$_2$ under vacuum, and evaporated to give a crude orange solid (0.47 g). This was purified by SiO$_2$ chromatography (hexane:EtOAc, 8:2, with 1% Et$_3$N, as eluent) to give 8 as an orange solid (0.105 g, 27%): $^1$H NMR (700 MHz, CDCl$_3$) δ 1.21/1.23 (s, 6H), 1.28 (s, 6H,), 1.66-1.71 (m, 2H), 3.19-3.24 (m, 2H), 3.92 (s, 3H), 4.15 (hept, J=6.6 Hz, 1H), 6.64 (d, J=8.7 Hz, 1H), 7.24-7.25 (m, 1H), 7.36 (d, J=1.8 Hz, 1H), 7.54 (d, J=8.3 Hz, 2H), 7.98 (d, J=8.3 Hz, 2H); $^{13}$C NMR (151 MHz, CDCl$_3$) δ 19.1, 30.1, 32.2, 36.7, 36.8, 47.4, 52.3, 86.8, 95.2, 108.0, 110.6, 128.5, 129.5, 129.6, 131.1, 131.2, 131.7, 145.0, 167.0; MS (ES):m/z=362.2 [M+H]$^+$; HRMS (ES) calcd. for C24H28NO2 [M+H]$^+$: 362.2120. found: 362.2114.

3(b) 4-2-[4,4-Dimethyl-1-(propan-2-yl)-1,2,3,4-tetrahydroquinolin-6-yl]ethynylbenzoic acid (9)

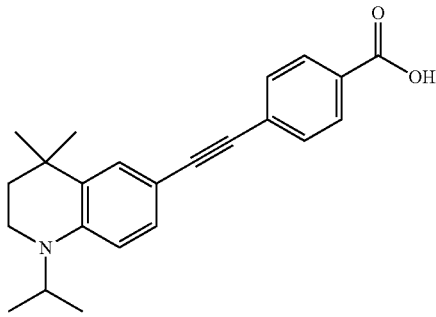 [SMILES: CC(C)N1CCC(C)(C)c2cc(C#Cc3ccc(C(=O)O)cc3)ccc21]

An oven-dried Schlenk flask was evacuated under reduced pressure and refilled with Ar, before Pd(PPh$_3$)$_2$Cl$_2$ (0.253 g, 0.36 mmol), CuI (0.0686 g, 0.36 mmol) and 7 (0.634 g, 3.96 mmol) were added and the flask sealed with a septum. A solution of 4 (1.185 g, 1.06 mmol) in triethylamine (30 mL) was degassed by sonication under vacuum, and backfilling with Ar (3×). This solution was then added to the Schlenk flask, degassed under vacuum and backfilled with Ar once more, and the resultant mixture stirred at RT for 72 h. The reaction mixture was then evaporated to dryness, and eluted through a thin Celite/SiO$_2$ plug with hexane, and then hexane:EtOAc (9:1). The organics were then washed with sat. NH$_4$Cl, 3% aq. EDTA, H$_2$O and brine, dried (MgSO$_4$) and evaporated to give an orange solid (1.38 g). This was dissolved in THF (30 mL) and aq. 20% NaOH (3 mL) was added. The resultant solution was stirred at reflux for 40 h, whereupon the mixture was cooled and H$_2$O added. The solution was neutralised with 5% HCl, diluted with EtOAc, washed with sat. NaHCO$_3$, H$_2$O and brine, dried (MgSO$_4$) and evaporated to give a crude yellow solid (1.0 g). This was recrystallised twice by solvent layering (DCM/hexane) to give 17 as bright yellow needles (0.73 g, 58% over two steps): $^1$H NMR (700 MHz; (CD$_3$)$_2$SO) δ 1.16 (s, 3H), 1.17 (s, 3H), 1.22 (s, 6H), 1.60-1.64 (m, 2H), 3.17-3.21 (m, 2H), 4.15 (hept, J=7.0 Hz, 1H), 6.70 (d, J=9.3 Hz, 1H), 7.19 (dd, J=8.6, 2.1 Hz, 1H), 7.30 (d, J=2.1 Hz, 1H), 7.56 (d, J=8.5 Hz, 2H), 7.92 (d, J=8.6 Hz, 2H), 13.02 (s, 1H); $^{13}$C NMR (700 MHz, (CD$_3$)$_2$SO) δ 18.6, 29.7, 31.6, 35.8, 36.1, 46.7, 86.6, 94.9, 106.5, 109.5, 110.5, 128.9, 129.4, 130.7, 130.7, 131.2, 144.7, 166.8; MS (ES):m/z=348.2 [M+H]$^+$; HRMS (ES) calcd. for C$_{23}$H$_{26}$NO$_2$ [M+H]$^+$: 348.1964. found: 348.1965.

Example 4

3-[4-(1,4,4-Trimethyl-1,2,3,4-tetrahydroquinolin-6-yl)-phenyl]-acrylic acid methyl ester (13)

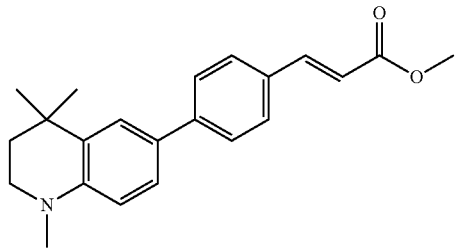 [SMILES: COC(=O)/C=C/c1ccc(-c2ccc3c(c2)C(C)(C)CCN3C)cc1]

4(a) Methyl-(3-methyl-but-2-enyl)-phenyl-amine

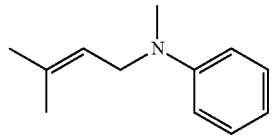

In a 500 mL round bottomed flask a solution of N-methylanaline (3.24 g, 30.32 mmol), 1-bromo-3-methyl-but-2-ene (5.0 g, 33.56 mmol) and K$_2$CO$_3$ (4.63 g, 33.56 mmol) in 160 ml MeCN was heated at 85° C. for 18 h at which time analysis via in situ ES$^+$-MS showed the reaction to be complete. The mixture was diluted with Et$_2$O (100 mL) and washed with H$_2$O (3×100 mL). The organic layer was dried with MgSO$_4$, filtered and evaporated in vacuo to give a crude oil which was filtered through a silica pad, eluting with hexane. The solvent was removed in vacuo to give the title compound as a clear oil (3.82 g, 72%); m/z (ES$^+$-MS) 176 (MH$^+$); $^1$H NMR (499.76 MHz, CDCl$_3$) δ 7.28 (2H, d, J=7.0 Hz), 6.79 (2H, d, J=7.0 Hz), 6.75 (1H, tr, J=7.0 Hz), 5.25 (1H, tr, J=6.0 Hz), 3.93 (2H d, J=6.0 Hz), 2.93 (3H, s) 1.76 (6H, s); $^{13}$C{$^1$H} NMR (100.61 MHz, CDCl$_3$) δ 149.86, 134.54, 129.08, 120.91, 116.42, 112.97, 50.53, 37.91, 25.70. 17.92; HRMS calcd for C$_{12}$H$_{18}$N ([M+H]$^+$) 176.14338. found 176.14336.

4(b) 1,4,4-Trimethyl-1,2,3,4-tetrahydroquinoline

In a 500 mL round bottomed flask a mixture of methyl-(3-methyl-but-2-enyl)-phenyl-amine (18.0 g, 102.86 mmol) and polyphosphoric acid (75 mL) was heated at 120° C. for 18 h, at which time analysis of purified aliquot of the mixture via $^1$H NMR spectroscopy showed the reaction to be complete. The mixture was diluted by the slow addition of H$_2$O (100 mL) over 5 minutes. The solution was cautiously basified via the addition of aqueous KOH and then extracted with Et$_2$O (1 L). The organic layer was washed with H$_2$O (3×200 mL), dried with MgSO$_4$, filtered and the solvent removed in vacuo to give a crude oil which was filtered through a silica pad, eluting with hexane. The solvent was removed in vacuo to give the title compound as a clear oil (14.93 g, 83%); m/z (EI-MS) 175 (50%, M$^+$), 160 (60%, M$^+$-Me); $^1$H NMR (499.76 MHz, CDCl$_3$) δ 7.23 (1H, dd, J=7.5, 1.5 Hz), 7.11 (1H, triplet of doublets, J=7.5, 1.5 Hz), 6.63 (1H, triplet of doublets, J=7.5, 1.5 Hz), 6.62 (1H, d, J=7.5 Hz), 3.25 (2H, tr, J=6.0 Hz), 2.92 (3H, s), 1.80 (2H, tr, J=6.0 Hz); $^{13}C\{^1H\}$ NMR (125.67 MHz, CDCl$_3$) δ 145.74, 131.61, 126.94, 126.02, 116.25, 111.09, 47.88, 39.50, 37.50, 32.19, 31.21, HRMS calcd for $C_{12}H_{18}N$ ([M+H]$^+$) 176.14338. found 176.14332.

4(c)
6-Iodo-1,4,4-trimethyl-1,2,3,4-tetrahydroquinoline

To a solution of 1,4,4-trimethyl-1,2,3,4-tetrahydro-quinoline (2.10 g, 12.0 mmol) and iodine (3.05 g, 12.0 mmol) in DCM (100 mL) was added red HgO (2.59 g, 12.0 mmol). The reaction was stirred at room temperature until analysis via $^1H$ NMR showed the reaction to be complete (2 h). The mixture was filtered, washed with dilute aqueous Na$_2$S$_2$O$_3$ (100 mL) and H$_2$O (100 mL). The organic layer was dried with MgSO$_4$ and the solvent removed in vacuo. The residue was filtered through an alumina plug, eluting with DCM and the solvent removed in vacuo to give the title compound as a pale yellow oil (2.50 g, 69%); m/z (EI-MS) 301 (100%, M$^+$), 286 (80%, M$^+$-Me); $^1H$ NMR (499.67 MHz, CDCl$_3$) δ 7.40 (1H, d, J=2.0 Hz), 7.32 (1H, dd, J=8.5, 2.0 Hz), 6.35 (1H, d, J=8.5 Hz), 3.24 (2H, tr, J=6.0 Hz), 2.89 (3H, s), 1.74 (2H, tr, J=6.0 Hz) 1.27 (6H, s); $^{13}C\{^1H\}$ NMR (125.67 MHz, CDCl$_3$) δ 144.92, 135.49, 134.34, 127.22, 126.52, 113.35, 47.58, 39.30, 36.87, 32.29, 30.79; HRMS calcd for $C_{12}H_{17}NI$([M+H]$^+$) 302.04003. found 302.04008.

4(d) 1,4,4-Trimethyl-6-(4,4,5,5-tetramethyl-[1,3,2]dioxaborolan-2-yl)-1,2,3,4-tetrahydroquinoline (12)

In a dry, N$_2$ filled glovebox, Pd(dppf)Cl$_2$ (0.126 g, 0.15 mmol), 6-iodo-1,4,4-trimethyl-1,2,3,4-tetrahydro-quinoline (0.93 g, 3.09 mmol), B$_2$pin$_2$ (0.78 g, 3.09 mmol) and KOAc (0.61 g, 6.18 mmol) were mixed in a thick walled glass tube fitted with a Young's tap. Degassed DMSO (10 mL) was added and the mixture heated at 80° C. for 18 h, at which time GCMS analysis showed the reaction to be complete. The mixture was diluted with Et$_2$O (100 mL) and washed with H$_2$O (3×100 mL). The organic layer was dried with MgSO$_4$, filtered and the solvent removed in vacuo to give a residue which was filtered through a silica pad, eluting with 1:1 DCM/hexane. Removal of the solvent in vacuo gave a crude product that was recrystallised from MeOH at −20° C. to give 12 as white needles (0.66 g 70%); mp 140-141° C.; m/z (EI-MS) 301 (100%, M$^+$), 286 (100%, M$^+$-Me); $^1H$ NMR (699.73 MHz, CDCl$_3$) δ 7.63 (1H, s) 7.55 (1H, d, J=8.0 Hz), 6.56 (1H, d, J=8.0 Hz), 3.29 (2H, tr, J=6.0 Hz), 2.94 (3H, s), 1.75 (2H, tr, J=6.0 Hz), 1.33 (12H, s), 1.31 (6H, s); $^{13}C\{^1H\}$ NMR (175.73 MHz, CDCl$_3$):

δ 147.8, 134.4, 132.3, 130.3, 110.1, 83.2, 47.7, 39.2, 37.2, 32.1, 30.7, 25.0, the resonance of the carbon attached to boron was not observed; $^{11}B\{^1H\}$ NMR (128.38 MHz, CDCl$_3$) δ 31.01; elemental analysis calcd. (%) for $C_{18}H_{28}BNO_2$: C 71.77, H 9.37, N 4.65. found: C 71.79, H 9.27, N 4.60.

4(e) 3-[4-(1,4,4-Trimethyl-1,2,3,4-tetrahydroquinolin-6-yl)-phenyl]-acrylic acid methyl ester (13)

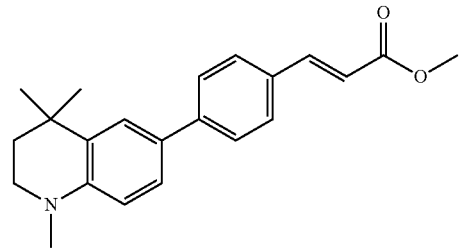 [SMILES: COC(=O)/C=C/c1ccc(-c2ccc3c(c2)C(C)(C)CCN3C)cc1]

In a dry, N$_2$ filled glovebox, Pd(dppf)Cl$_2$ (25 mg, 0.03 mmol), 1,4,4-trimethyl-6-(4,4,5,5-tetramethyl-[1,3,2]dioxaborolan-2-yl)-1,2,3,4-tetrahydroquinoline (0.49 g, 1.55 mmol), 3-(4-bromo-phenyl)-acrylic acid methyl ester (0.37 g, 0.83 mmol) and K$_3$PO$_4$.2H$_2$O (0.77 g, 3.10 mmol) were mixed in a thick walled glass tube fitted with a Young's tap. Degassed $^i$PrOH (10 mL) and H$_2$O (1 mL) were added and the mixture heated at 80° C. for 18 h, at which time GCMS analysis showed the reaction to be complete. The solvent was removed in vacuo and the residue dissolve in DCM (100 mL) and washed with H$_2$O (3×20 mL). The organic layer was dried with MgSO$_4$, filtered and the solvent removed in vacuo to give a residue which was filtered through a silica pad, eluting with DCM. Removal of the solvent in vacuo gave a yellow solid which was recrystallised from MeOH at −20° C. to give yellow white needles of 13 (0.32 g, 62%); mp 121-123° C.; UV-vis (CHCl$_3$) $\lambda_{max}$ (ε) 380 nm (23900 L mol$^{-1}$ cm$^{-1}$); $\lambda_{em}$ (CHCl$_3$) 536 nm; m/z (ES$^+$-MS) 336 ([M−H]$^+$); $^1H$ NMR (499.77 MHz, CDCl$_3$) δ 7.73 (1H, d, J=16.0 Hz), 7.58 (2H, d, J=8.5 Hz), 7.56 (2H, d, J=8.5 Hz), 7.48 (1H, s), 7.37 (1H, d, J=8.0 Hz), 6.66 (1H, d, J=8.0 Hz), 6.45 (1H, d, J=16.0 Hz), 3.83 (3H, s), 3.30 (2H, tr, J=5.5 Hz), 2.97 (3H, s), 1.81 (2H, tr, J=5.5 Hz), 1.35 (6H, s); $^{13}C\{^1H\}$ NMR (125.67 MHz, CDCl$_3$) δ 167.87. 145.49, 144.98, 143.89, 131.85 (2 peaks overlapped), 12.71, 127.45, 126.49, 125.63, 124.56, 116.56, 111.28, 51.79, 47.75, 39.40, 37.24, 32.34, 30.97; HRMS calcd for $C_{22}H_{26}NO_2$ ([M−H]$^+$) 336.19581. found 336.19577.

Example 5

6-(1,4,4-Trimethyl-1,2,3,4-tetrahydroquinolin-6-yl)-naphthalene-2-carboxylic acid methyl ester (11)

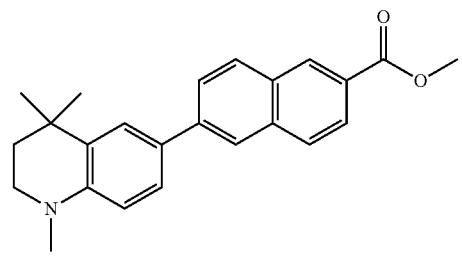 [SMILES: COC(=O)c1ccc2cc(-c3ccc4c(c3)C(C)(C)CCN4C)ccc2c1]

5(a) 6-(5,5-Dimethyl-[1,3,2]dioxaborinan-2-yl)-1,4,4-trimethyl-1,2,3,4-tetrahydroquinoline (10)

In a dry, N$_2$ filled glovebox, Pd(dppf)Cl$_2$ (0.135 g, 0.17 mmol), 6-iodo-1,4,4-trimethyl-1,2,3,4-tetrahydro-quinoline (1.0 g, 3.32 mmol), B₂pin₂ (0.75 g, 3.32 mmol) and KOAc (0.65 g, 6.64 mmol) were mixed in a thick walled glass tube fitted with a Young's tap. Degassed DMSO (10 mL) was added and the mixture heated at 80° C. for 18 h, at which time GCMS analysis showed the reaction to be complete. The mixture was diluted with Et₂O (100 mL) and washed with H₂O (3×100 mL). The organic layer was dried with MgSO₄, filtered and the solvent removed in vacuo to give a residue which was filtered through a silica pad, eluting with 1:1 DCM/hexane. Removal of the solvent in vacuo gave a crude product that was recrystallised from MeOH at −20° C. to give white needles of 10 (0.80 g, 88%); mp 151-153° C.; m/z (EI-MS) 287 (90%, M⁺), 272 (100%, M⁺-Me); ¹H NMR (499.77 MHz, CDCl₃) δ 7.64 (1H, d, J=1.5 Hz), 7.54 (1H, dd, J=8.5, 1.5 Hz), 7.27 (1H, s), 6.57 (1H, d, J=8.5 Hz), 3.75 (4H, s), 3.28 (2H, tr, J=6.0 Hz), 2.94 (3H, s), 1.76 (2H, tr, J=6.0 Hz), 1.32 (6H, s), 1.02 (6H, s); ¹³C{¹H} NMR (125.67 MHz, CDCl₃) δ 147.49, 133.29, 131.42, 130.19, 110.09, 72.33, 47.75, 39.24, 37.29, 32.05, 32.03, 30.83, 20.12, the resonance of the carbon attached to boron was not observed; ¹¹B{¹H} NMR (128.38 MHz, CDCl₃) δ 27.02; elemental analysis calcd. (%) for C₁₇H₂₆BNO₂: C 71.09, H 9.12, N 4.88. found: C 71.00, H 9.12, N 4.81.

5(b) 6-(1,4,4-Trimethyl-1,2,3,4-tetrahydroquinolin-6-yl)-naphthalene-2-carboxylic acid methyl ester, (11)

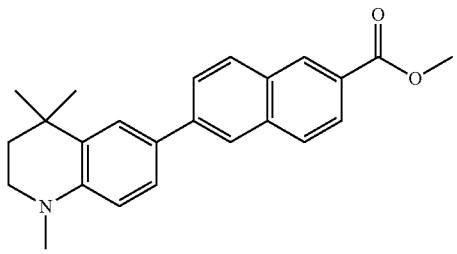 [SMILES: COC(=O)c1ccc2cc(-c3ccc4c(c3)C(C)(C)CCN4C)ccc2c1]

In a dry, N₂ filled glovebox, Pd(dppf)Cl₂ (13 mg, 0.02 mmol), 6-(5,5-dimethyl-[1,3,2]dioxaborinan-2-yl)-1,4,4-trimethyl-1,2,3,4-tetrahydro-quinoline (0.25 g, 0.87 mmol), 6-bromo-naphthalene-2-carboxylic acid methyl ester (0.22 g, 0.83 mmol) and K₃PO₄.2H₂O (0.43 g, 1.74 mmol) were mixed in a thick walled glass tube fitted with a Young's tap. Degassed DMSO (15 mL) and H₂O (3 mL) were added and the mixture heated at 80° C. for 18 h, at which time GCMS analysis showed the reaction to be complete. The mixture was diluted with Et₂O (100 mL) and washed with H₂O (3×100 mL). The organic layer was dried with MgSO₄, filtered and the solvent removed in vacuo to give a residue which was filtered through a silica pad, eluting with DCM. Removal of the solvent in vacuo gave a yellow solid which was recrystallised from MeOH at −20° C. to give yellow white needles of 11 (0.28 g, 94%); mp 166-167° C.; UV-vis (CHCl₃) λ$_{max}$ (E) 243 nm (53200 L mol⁻¹ cm⁻¹); λ$_{em}$ (CHCl₃) 494 nm; m/z (EI-MS) 359 (100%, M⁺), 344 (60%, M+−Me); ¹H NMR (699.73 MHz, CDCl₃) δ 8.60 (1H, s), 8.06 (1H, dd, J=8.5, 1.5 Hz), 7.99 (1H, s), 1.97 (1H, d, J=8.5 Hz), 7.90 (1H, d, J=8.0 Hz), 7.81 (1H, dd, J=8.5, 1.5 Hz), 7.60 (1H, d, J=2.0 Hz), 7.49 (1H, dd, J=8.5, 2.0 Hz), 6.71 (1H, d, J=8.5 Hz), 3.99 (3H, s), 3.32 (2H, tr, J=6.0 Hz), 2.99 (3H, s), 1.84 (2H, tr, J=6.0 Hz), 1.39 (6H, s); ¹³C{¹H} NMR (175.73 MHz, CDCl₃) δ 167.55, 145.49, 141.72, 136.29, 131.99, 131.08, 129.74, 128.74, 128.18, 126.62, 126.31, 126.05, 125.62, 124.97, 123.74, 111.41, 52.29, 47.79, 39.43, 37.31, 32.40, 31.03; HRMS calcd for C₂₄H₂₅NO₂ (M⁺) 359.18798. found 359.18789.

Example 6

4-2-[2,4,4-Trimethyl-1-(propan-2-yl)-1,4-dihydro-quinolin-6-yl]ethynylbenzoic acid, (17)

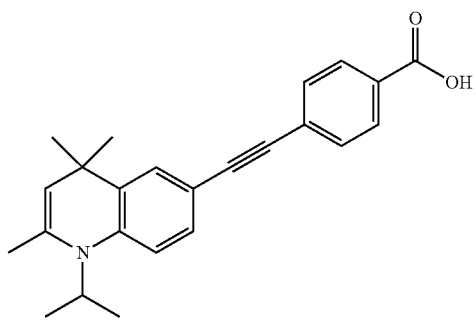 [SMILES: CC1=CC(C)(C)c2cc(C#Cc3ccc(C(=O)O)cc3)ccc2N1C(C)C]

6(a) 6-Iodo-2,4,4-trimethyl-1-(propan-2-yl)-1,4-dihydroquinoline, (15)

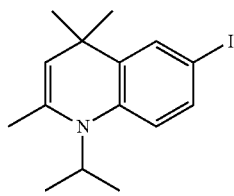 [SMILES: CC1=CC(C)(C)c2cc(I)ccc2N1C(C)C]

To a solution of 3 (1.17 g, 3.42 mmol) in anhydrous THF (50 mL) was added MeMgBr (3.0 M in Et₂O, 2.28 mL, 6.84 mmol) and the resultant solution stirred at reflux for 16 h. The solution was cooled, quenched with 20% HCl (1.14 mL) and H₂O, diluted with EtOAc, washed with H₂O and brine, dried (MgSO₄) and evaporated to give a crude colourless oil (0.95 g). This was immediately purified by SiO₂ chromatography (hexane:EtOAc, 97.5:2.5, with 1% Et₃N, as eluent) to give 15 as a pink oil (0.35 g, 30%) which was immediately used in the next reaction: ¹H NMR (400 MHz, CDCl₃) δ 1.20 (s, 6H), 1.45 (s, 3H), 1.46 (s, 3H), 1.98 (d, J=0.9 Hz, 3H), 4.16 (hept, J=7.1 Hz, 1H), 4.50 (q, J=1.2 Hz, 1H), 6.73 (d, J=8.7 Hz, 1H,), 7.34 (dd, J=8.7, 2.2 Hz, 1H), 7.42 (d, J=2.1 Hz, 1H).

6(b) 4-2-[2,4,4-Trimethyl-1-(propan-2-yl)-1,4-dihydroquinolin-6-yl]ethynyl benzoic acid, (17)

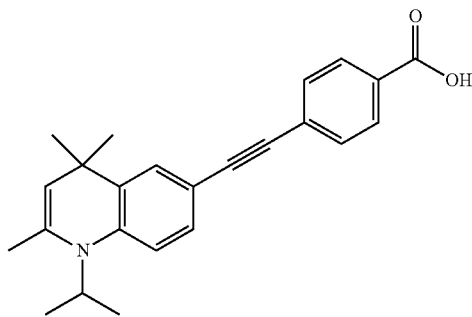 [SMILES: CC1=CC(C)(C)c2cc(C#Cc3ccc(C(=O)O)cc3)ccc2N1C(C)C]

Pd(PPh$_3$)$_2$Cl$_2$ (0.073 g, 0.104 mmol), CuI (0.0198 g, 0.104 mmol) and 7 (0.176 g, 1.10 mmol) were added to a Schlenk flask under Ar. The flask was evacuated and refilled with Ar. 15 (0.356 g, 1.04 mmol), dissolved in triethylamine (12 mL), was added and the flask evacuated/filled with Ar again (3×). The mixture was stirred at RT for 72 h. The solution was diluted with Et$_2$O, passed through Celite/SiO$_2$ under vacuum, and evaporated to give a crude green solid (0.4 g). This was purified by SiO$_2$ chromatography (hexane: EtOAc, 8:2, with 1% Et$_3$N, as eluent) to give 16 (scheme IV) as a pale green solid (0.12 g, 30%). 16 (0.073 g, 0.195 mmol) was then dissolved in THF (10 mL), and to this was added aq. 20% NaOH (2 mL). The resultant solution was stirred at reflux for 40 h, whereupon the mixture was cooled and H$_2$O and Et$_2$O added. The solution was acidified to pH 7 with 5% HCl, diluted with Et$_2$O, washed with brine, dried (MgSO$_4$) and evaporated to give 17 as a yellow solid (0.070 g, 99%): $^1$H NMR (400 MHz; CDCl$_3$) δ 1.24 (s, 6H), 1.47 (s, 3H), 1.49 (s, 3H), 2.01 (d, J=0.9 Hz, 3H), 4.23 (hept, J=7.2 Hz, 1H), 4.53 (d, J=1.1 Hz, 1H), 6.93 (d, J=8.6 Hz, 1H), 7.27-7.29 (m, 1H), 7.37 (d, J=2.0 Hz, 1H), 7.54 (d, J=8.3 Hz, 2H), 8.03 (d, J=8.4 Hz, 2H).

Example 7

Initial Fluorescence Characterisation of Compound 9 of Example 3 and Compound 17 of Example 6

Figure 1:
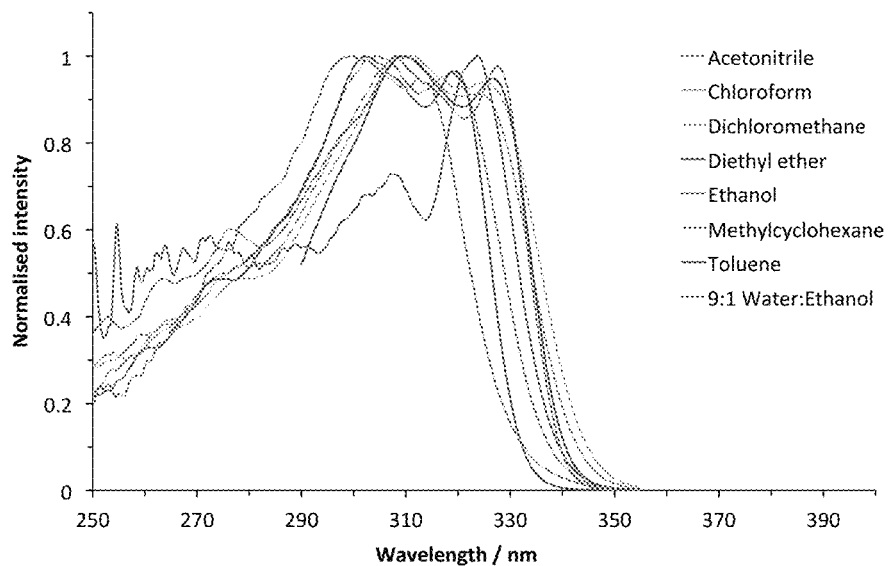
FIG. 1 illustrates normalised excitation spectra of EC23® in a range of solvents.
Figure 2:
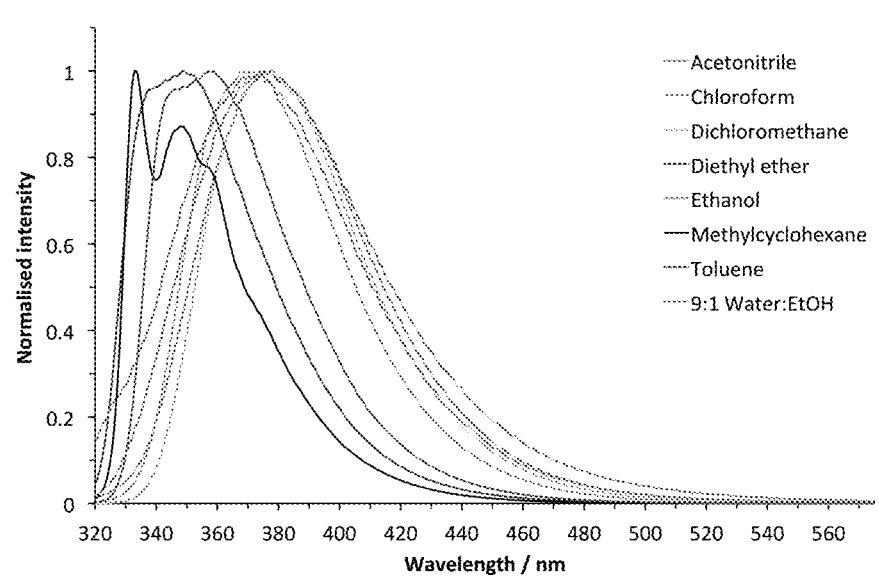
FIG. 2 illustrates normalised emission spectra of EC23® in a range of solvents, with excitation at 300 nm.
Figure 3:
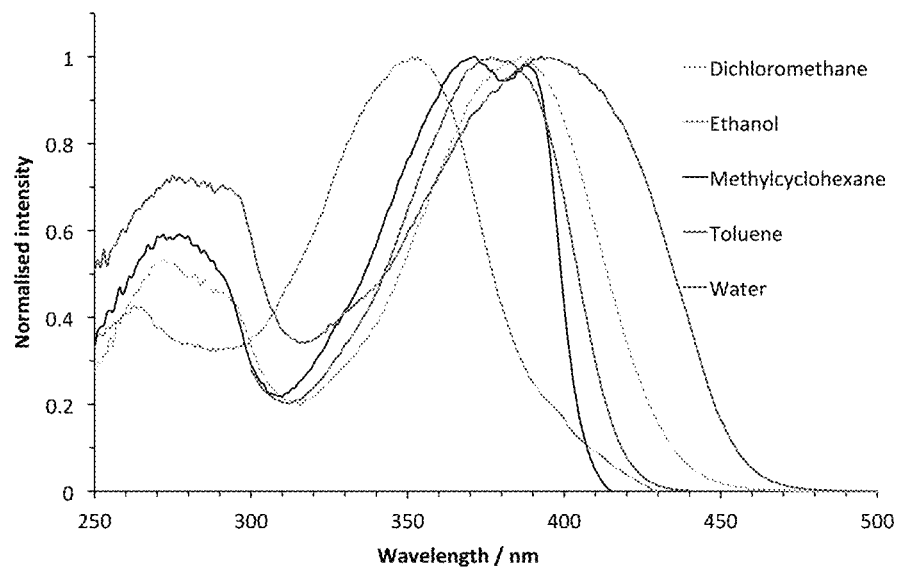
FIG. 3 illustrates normalised excitation spectra of compound 9 of Example 3 in a range of solvents.
Figure 4:
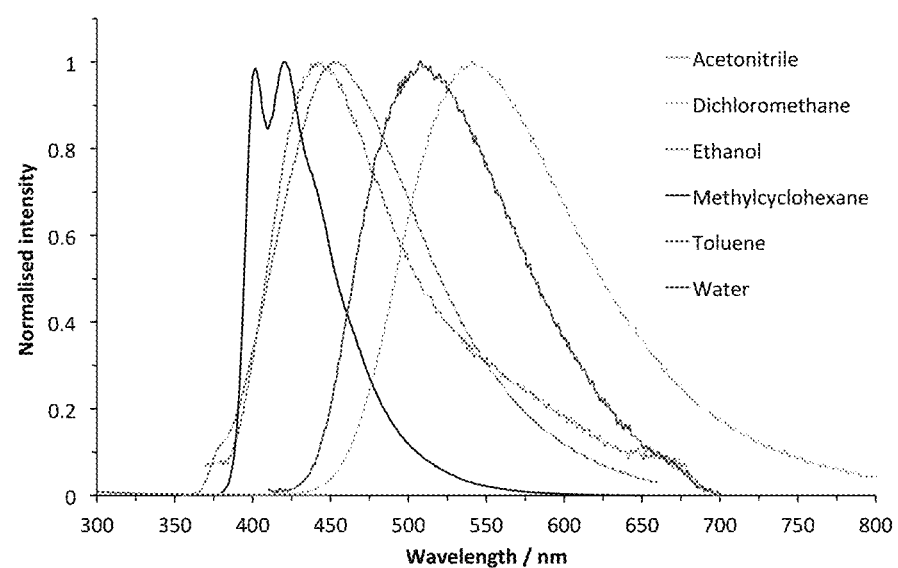
FIG. 4 illustrates normalised emission spectra of compound 9 of Example 3 in a range of solvents, with excitation in the range of 275-300 nm.

Absorption and emission spectra of 9 were obtained in a variety of solvents (FIG. 3 and FIG. 4). Comparison of 9 with EC23® (FIG. 1 and FIG. 2) shows significant increases in the maximal absorption and emission wavelengths. The fluorescence from 9 was easily detected at concentrations as low as 1 nM, and solvent-dependent effects were observed, with high intensity fluorescence detected in non polar solvents, while significant fluorescence quenching was observed in water, in particular. The fluorescence emission wavelength is also highly dependent on solvent polarity, with a significant red shift occurring in polar solvents when compared to non polar solvents. This initial characterisation indicated that when applied to cells, the fluorescence of 9 could be expected to be discernable in discrete cellular locations, depending on the local polarity.

Figure 5:
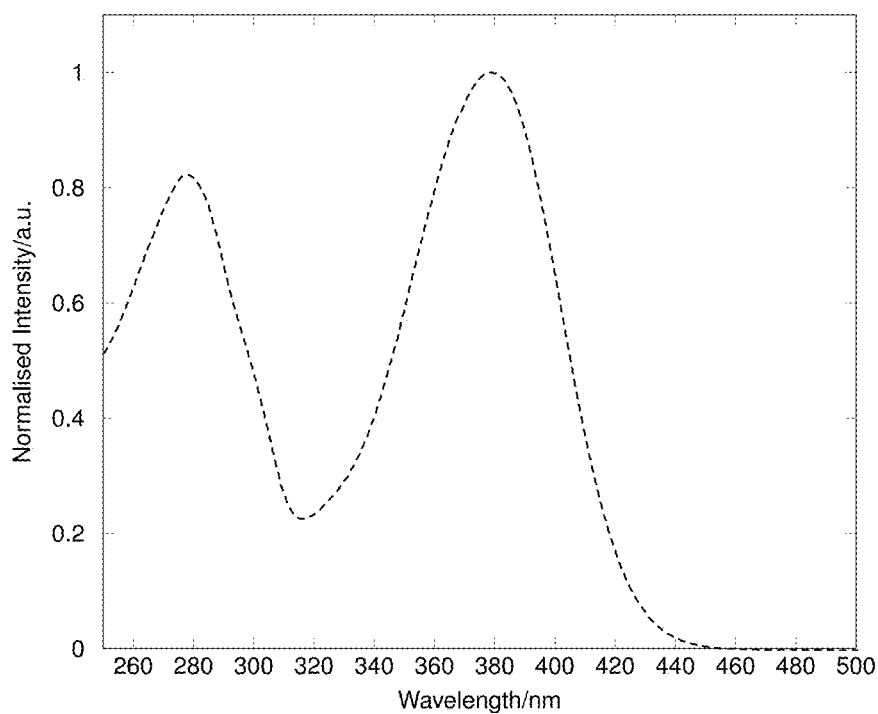
FIG. 5 illustrates the normalised excitation spectrum of compound 17 of Example 6 in chloroform.
Figure 6:
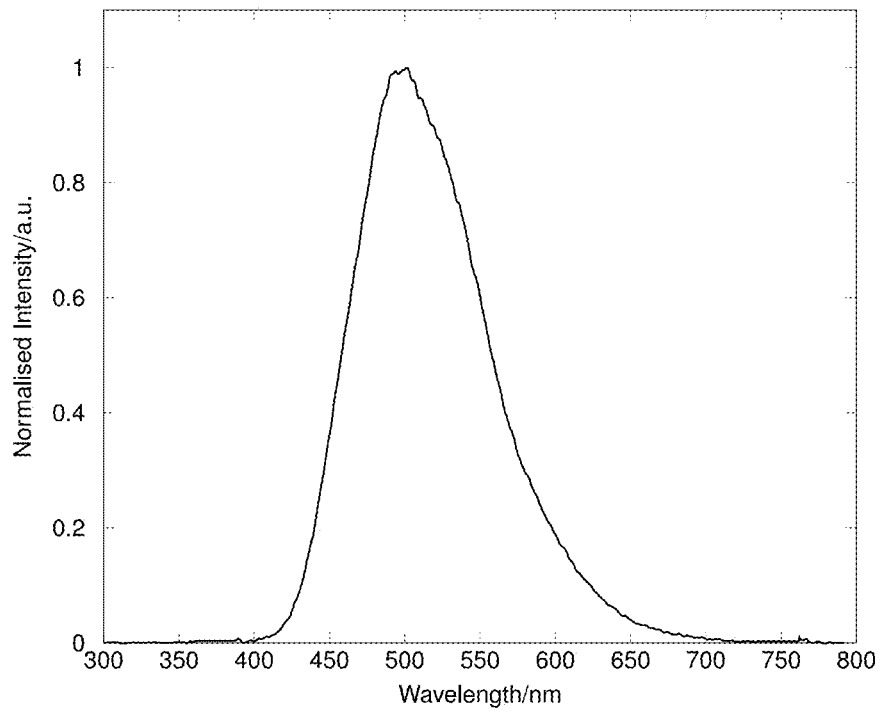
FIG. 6 illustrates the normalised emission spectrum of compound 17 of Example 6 in chloroform, with excitation at 378 nm.

Compound 17 exhibits a similar emission profile to compound 9 (FIG. 6), but also exhibits a longer maximal absorption wavelength (FIG. 5). This absorption band peaks at around 379 nm, and trails into the indigo/blue (440 nm). This longer wavelength absorption band indicates that compound 17 will be more effectively excited than compound 9 with the 405 nm excitation source that is typical on fluorescence microscopes.

Light Stability of Compound 9 of Example 3

Figure 7:
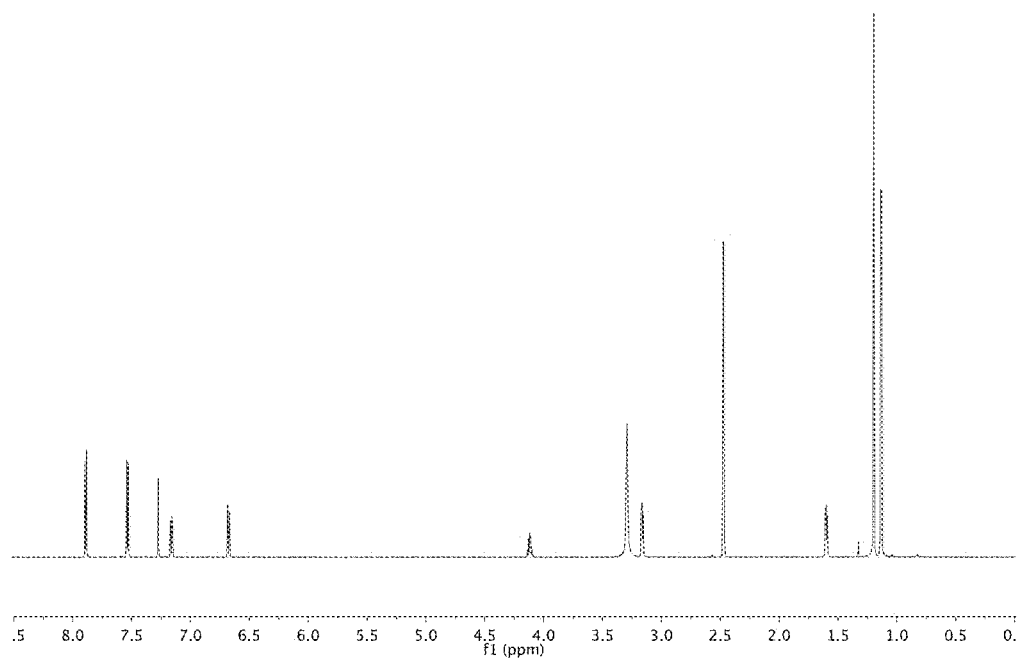
FIG. 7 illustrates a $^1$H NMR spectrum of compound 9 of Example 3 after storage at ambient temperature in the absence of light.
Figure 8:
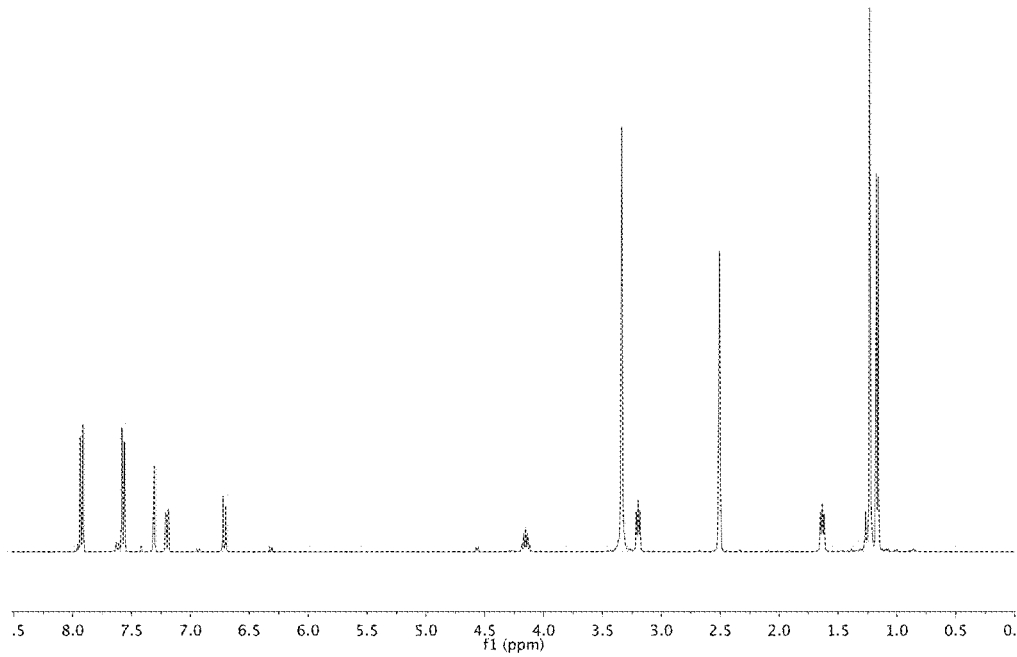
FIG. 8 illustrates a $^1$H NMR spectrum of compound 9 of Example 3 after treatment with typical laboratory light for 72 hours at ambient temperature.

A $^1$H NMR spectrum of compound 9 in DMSO-d$_6$ was recorded after storage at ambient temperature in the absence of light (FIG. 7). The same sample of compound 9 was then exposed to standard laboratory light at a distance of 30 cm for 72 hours, and the $^1$H NMR spectrum recorded (FIG. 8). Compound 9 is stable towards typical laboratory lighting over this time period, although a small proportion converts to a structurally similar enamine form. Compound 9 remains stable until around 16 day's exposure, where some indication of degradation becomes apparent. More significant degradation is observed after 22 day's exposure, although compound 9 still represents the major constituent of the sample (>60%).

Biological Evaluation of Compound 9 and Compound 17

Defining properties of retinoids are their ability to induce differentiation of specific cell types and to induce the expression of genes which are directly responsive to retinoic acid by being linked to DNA of defined sequences (retinoic acid response elements, RAREs) which binds ligand-activated retinoic acid receptors (RARs), thus enabling recruitment of the gene transcription machinery to the gene regulatory sequences (promoter) necessary for messenger RNA transcripts of the gene to be expressed.

To show that the fluorescent retinoids exhibit retinoid activity, TERA-2 cells (an embryonal carcinoma cell line) were treated with 1 and 10 M ATRA, EC23® and compound 9, and the resultant samples stained with a variety of immunocytochemical stains. FIG. 9 shows the result of the treatment of TERA-2 cells with 1 and 10 M ATRA, EC23® and compound 9, and with the vehicle solvent, DMSO, on the presence of nestin, an intermediate filament that is typically expressed in neural stem cells. All conditions were positive for nestin with staining possibly to a lesser extent in 10 μM EC23® and compound 9 samples.

Figure 10:
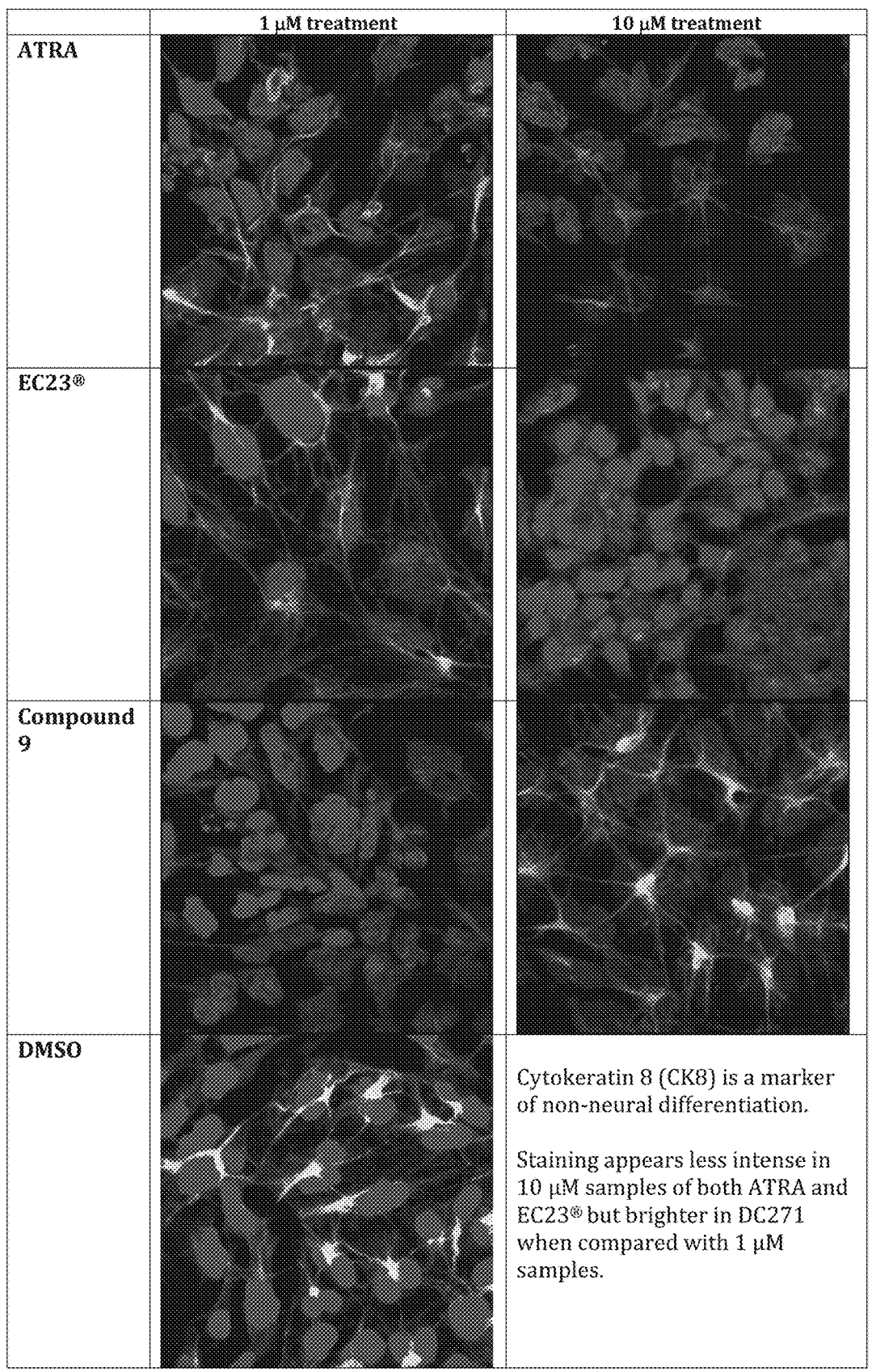
FIG. 10 illustrates compound 9 of Example 3 activity in stem cells compared to ATRA, EC23® and DMSO-CK8 staining.

FIG. 10 shows the result of the treatment of TERA-2 cells with 1 and 10 μM ATRA, EC23® and compound 9, and with the vehicle solvent, DMSO, on the presence of cytokeratin 8 (CK8), a marker of non-neural differentiation. The staining appears less intense in 10 μM samples of both ATRA and EC23®, as is typical with a reduction in non-neural differentiation, but slightly brighter with compound 9 when compared with 1 μM samples. DMSO treatment shows very bright staining for CK8.

Figure 11:
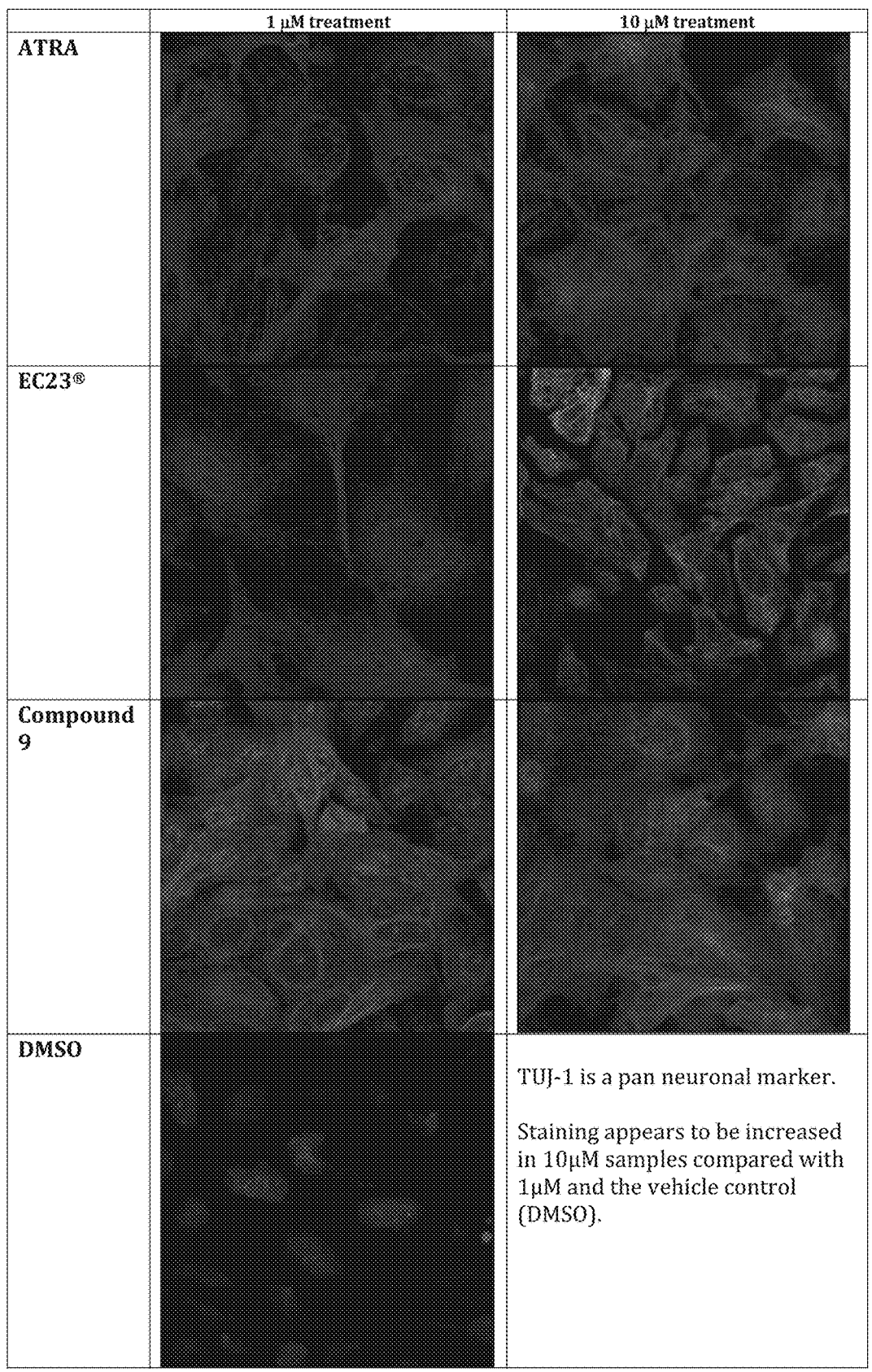
FIG. 11 illustrates compound 9 of Example 3 activity in stem cells compared to ATRA, EC23® and DMSO-TUJ-1 staining.

FIG. 11 shows the result of the treatment of TERA-2 cells with 1 and 10 μM ATRA, EC23® and compound 9, and with the vehicle solvent, DMSO, on the presence of TUJ-1, a pan neuronal marker. Samples treated with ATRA, EC23® and compound 9 show significant staining for TUJ-1, with increased staining evident with 10 μM treatment. DMSO treated cells show only limited TUJ-1 staining.

Figure 12:
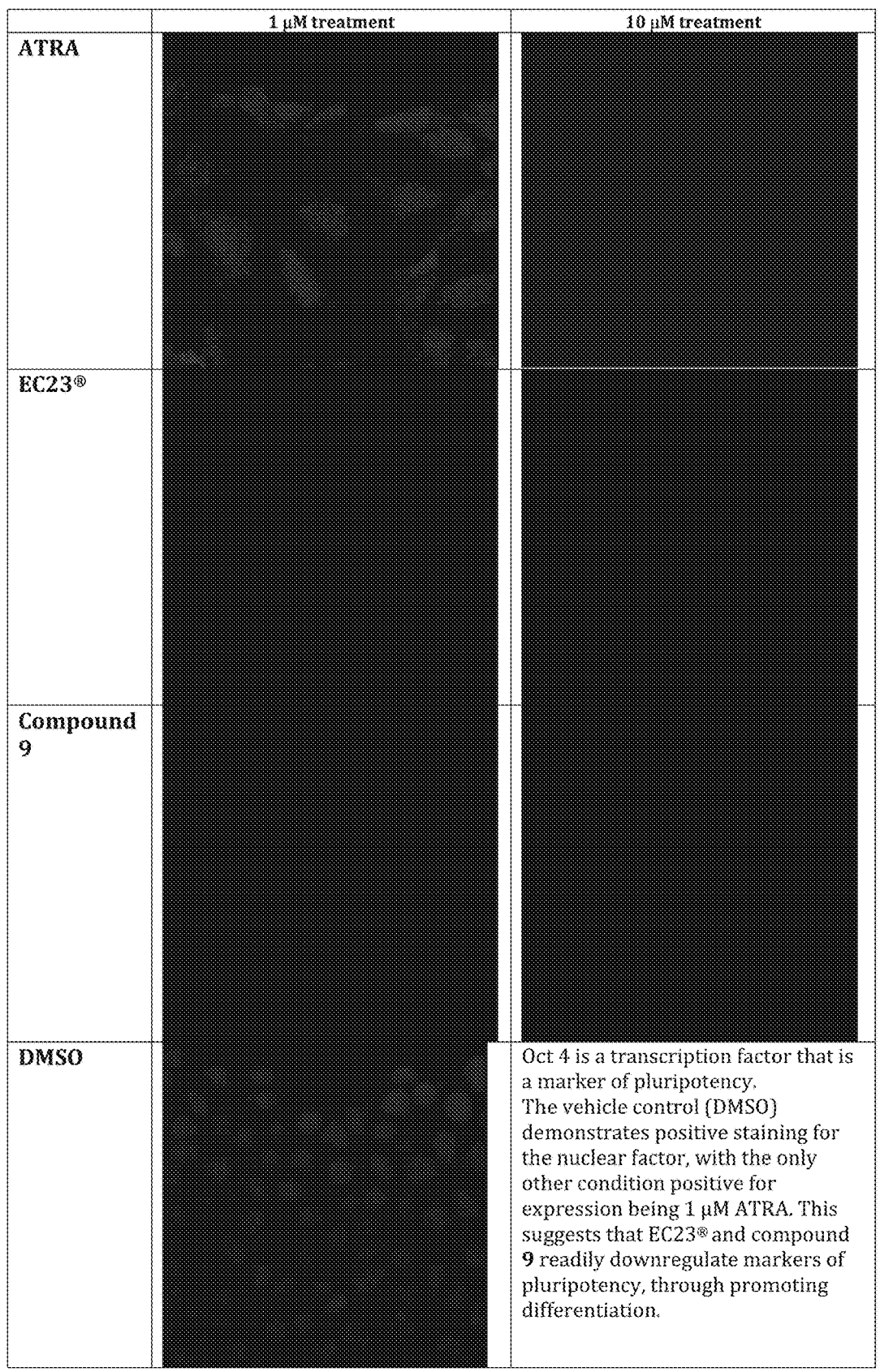
FIG. 12 illustrates compound 9 of Example 3 activity in stem cells compared to ATRA, EC23® and DMSO-Oct 4 staining.

FIG. 12 shows the result of the treatment of TERA-2 cells with 1 and 10 μM ATRA, EC23® and compound 9, and with the vehicle solvent, DMSO, on the presence of Oct 4, a transcription factor that is a marker of pluripotency. DMSO treated cells show obvious positive staining for Oct 4, and staining is also evident in 1 μM ATRA treatment. All other conditions do not exhibit staining for Oct 4, indicating that EC23® and compound 9 readily downregulate markers of pluripotency through the promotion of differentiation.

FIG. 13 shows the result of the treatment of TERA-2 cells with 1 and 10 μM ATRA, EC23® and compound 9, and with the vehicle solvent, DMSO, on the presence of Sox 2, a transcription factor that is a marker of pluripotency. DMSO treated cells show obvious positive staining for Sox 2, with significantly reduced staining in cells treated with ATRA, EC23® and compound 9. This observations suggests that ATRA, EC23® and compound 9 readily downregulate markers of pluripotency through the promotion of differentiation.

FIG. 14 shows flow cytometric analysis of TERA-2 cells treated with ATRA, EC23® and compound 9, and DMSO. The expression of stem cell marker SSEA-3 is measured, which is generally reduced when cells are treated with retinoids. SSEA-3 flow cytometry shows that expression of SSEA-3 is significantly decreased in retinoid treated cells compared to DMSO treated cells. Compound 9 treated cells showed higher levels of SSEA-3 than ATRA and EC23® at both 1 and 10 M treatments.

FIG. 15 shows flow cytometric analysis of TERA-2 cells treated with ATRA, EC23® and compound 9, and DMSO. The expression of stem cell marker TRA160 is measured, which is generally reduced when cells are treated with retinoids. TRA160 flow cytometry shows that expression of TRA160 is significantly decreased in retinoid treated cells compared to DMSO treated cells. Compound 9 treated cells showed slightly higher levels of TRA160 than ATRA and EC23® at both 1 and 10 M treatments.

FIG. 16 shows flow cytometric analysis of TERA-2 cells treated with ATRA, EC23® and compound 9 and DMSO. The expression of early neuronal marker A2B5 is measured, which is generally increased when cells are treated with retinoids. A2B5 flow cytometry shows that expression of A2B5 is significantly increased in retinoid treated cells compared to DMSO treated cells. ATRA treated cells express higher levels of A2B5 followed by EC23® and compound 9.

FIG. 17 shows phase contrast images of cell populations that have been treated with ATRA, EC23® and compound 9, and DMSO. In cell populations treated with DMSO, the cells are small, and densely packed together. In contrast, cell populations treated with ATRA, EC23® and compound 9 are less dense, and cells are much more spread out.

FIG. 18 and FIG. 19 shows an MTT cell viability analysis of 1 and 10 μM treatments of ATRA, EC23® and compound 9, and DMSO. All treatments exhibit comparable viability to DMSO, suggesting cells treated with retinoids do not experience significant toxic effects.

Figure 20:
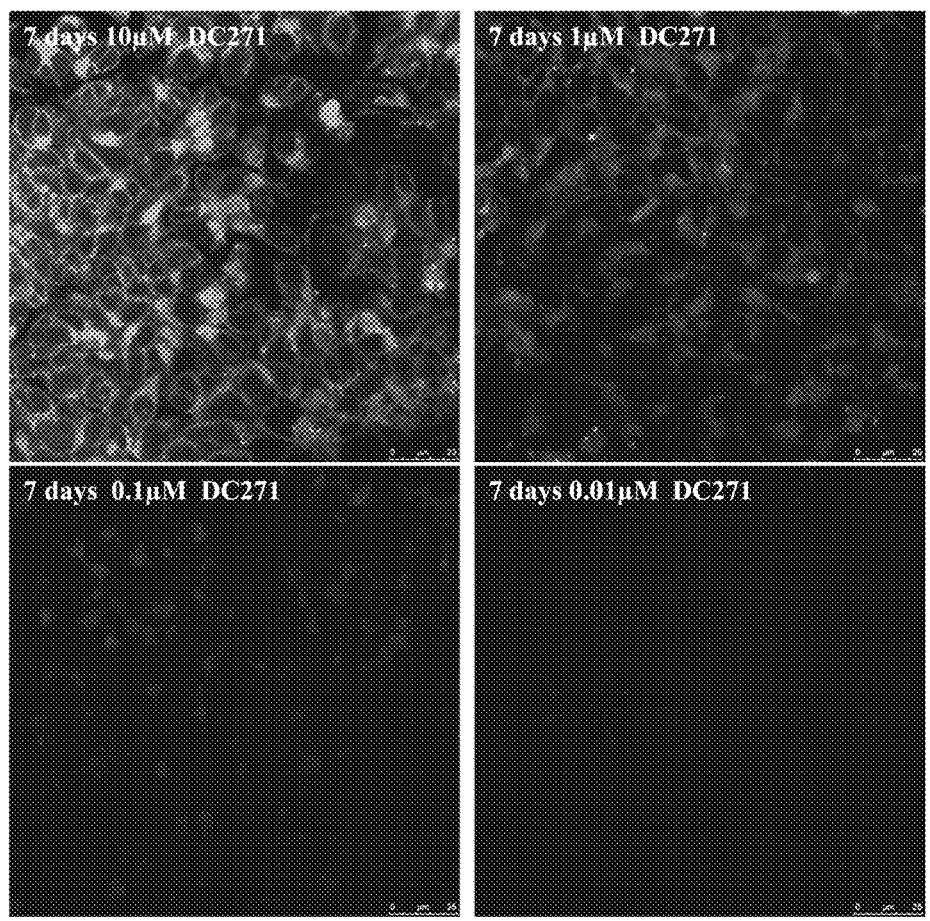
FIG. 20 illustrates TERA-2 stem cells treated with compound 9 over a range of concentrations, imaged using confocal microscopy after 7 days.

FIG. 20 shows TERA-2 cells treated with compound 9 at 10, 1, 0.1, 0.01 μM concentrations, and imaged using a confocal fluorescence microscope after 7 days. Even at the lowest treatment concentration, the fluorescence of compound 9 is visible, with 0.1-10 μM treatments easily imaged. Compound 9 is mainly localised around the nuclear envelope, and appears also to be localised around other cellular structures.

Figure 21:
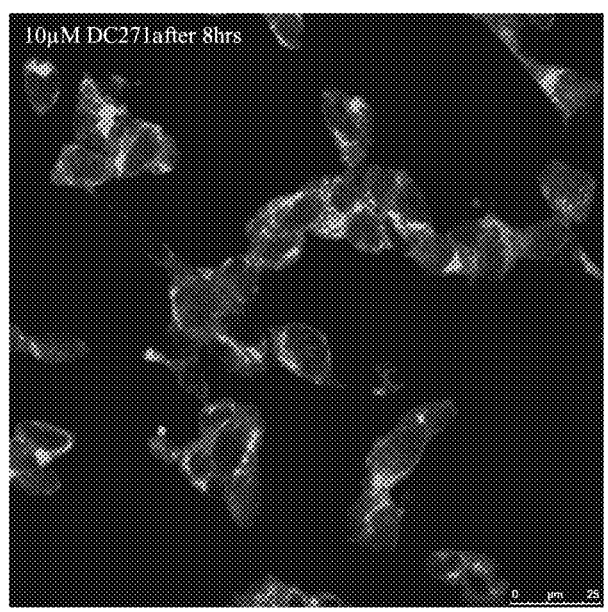
FIG. 21 illustrates SHSY5Y cells (neuroblastoma) treated with compound 9 of Example 3 (10 μM), and imaged using a confocal microscope after 8 hours.

FIGS. 21, 22 and 23 respectively show SHSY5Y cells (neuroblastoma) and fibroblast cells and TERA-2 cells treated with 10 μM compound 9, and imaged using a confocal fluorescence microscope after 8 hours (SHSY5Y) and 24 hours (fibroblasts) and 7 days (TERA-2). Compound 9 is again clearly visible with obvious localisation around the nuclear envelope.

FIG. 24 shows HaCat keratinocyte skin cells that were treated with 10 μM compound 9 for 5 days, fixed and then imaged with a confocal fluorescence microscope.

FIG. 25 shows HaCat keratinocyte skin cells treated with compound 9 (10 μM) for 5 days. The fixed coverslips were then stained with Involucrin (green) and K14 (red) and imaged using a confocal microscope. The fluorescence of compound 9 is coloured in blue. Involucrin selectively stains Cellular Retinoic Acid Binding Protein (CRABP), which transports retinoids in and around the nucleus. K14 is a prototypic marker of dividing basal keratinocytes and helps in the maintenance of epidermal cell shape.

FIG. 27 shows HaCat keratinocyte skin cells treated with compound 17 (10 μM) for 5 days. The fixed coverslips were then stained with Involucrin (green) and K14 (red) and imaged using a confocal microscope. The fluorescence of compound 17 is coloured in blue. Involucrin selectively stains Cellular Retinoic Acid Binding Protein (CRABP), which transports retinoids in and around the nucleus. K14 is a prototypic marker of dividing basal keratinocytes and helps in the maintenance of epidermal cell shape. As in FIG. 26, the fluorescence from compound 17 is significantly more intense than that exhibited by compound 9 under identical conditions (FIG. 25).

FIG. 28 shows the Raman spectrum of compound 9. A high intensity acetylene band is observed at 2190 cm$^{-1}$. This lies in the cellular silent region (1800-2800 cm$^{-1}$), wherein signals of biological origin, such as amide bonds, are not observed. This spectral separation allows Raman bands in the cellular silent region to be more easily detected when imaging or analysing cellular samples using Raman microscopy/spectroscopy.

The invention claimed is:

1. A compound of formula I:

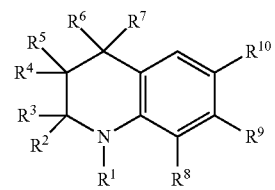

I in which $R^1$ is hydrogen, alkyl C1-10 or acyl;

$R^2$, $R^3$, $R^4$ and $R^5$, which may be the same or different, are each hydrogen or alkyl C1-4, or together one pair of $R^2$ and $R^4$ or $R^3$ and $R^5$ represent a bond;

$R^6$ and $R^7$, which may be the same or different, are each hydrogen, alkyl C1-4 or together one pair of $R^4$ and $R^6$ or $R^5$ and $R^7$ represent a bond, or $R^6$ and $R^7$ together form a group:
=$CR^{11}R^{12}$;

provided that the pair of $R^4$ and $R^6$ or $R^5$ and $R^7$ does not represent a bond if a pair from $R^2$, $R^3$, $R^4$ and $R^5$ represents a bond;

$R^8$ and $R^9$, which may be the same or different, are each hydrogen, alkyl C1-10, aryl, aralkyl, halogen, trifluoroalkyl, cyano, nitro, —NR$^a$R$^b$, —OR$^a$, —C(O)R$^a$, —C(O)OR$^a$, —OC(O)R$^a$, —S(O)R$^a$R$^b$, and —C(O)NR$^a$R$^b$;

$R^{11}$ and $R^{12}$, which may be the same or different, are each hydrogen or alkyl C1-10; and $R^a$ and $R^b$, which may be the same or different, are each hydrogen or alkyl C1-10;

$R^{10}$ is a group II, III, IV, V, VI, VII, VIII, IX, or XI:

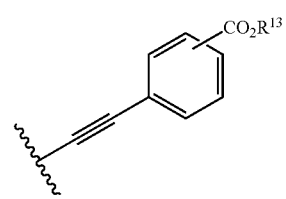

II

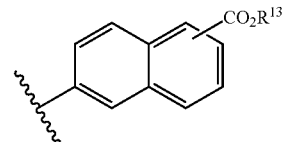

III

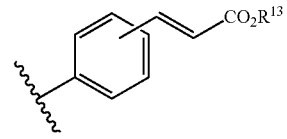

IV

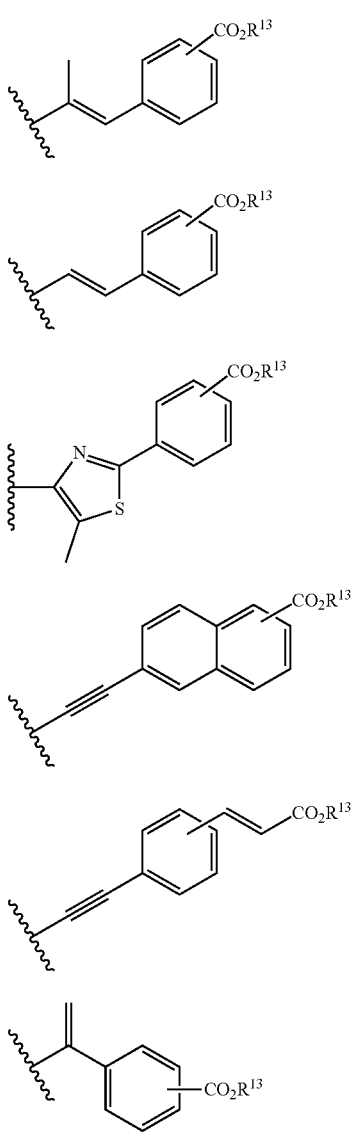

in which $R^{13}$ is hydrogen or alkyl C1-10;

with the proviso that when $R^{10}$ is a group II or a group V, one pair of $R^2$ and $R^4$, $R^3$ and $R^5$, $R^4$ and $R^6$ or $R^5$ and $R^7$ represent a bond;

and isomers thereof;

in free or in salt form.

2. The compound according to claim 1 in which $R^{10}$ is a group II, as defined in claim 1.

3. The compound according to claim 1 in which $R^{10}$ is a group III, as defined in claim 1.

4. The compound according to claim 1 in which $R^{10}$ is a group IV, as defined in claim 1.

5. The compound according to claim 1 in which $R^{10}$ is a group V, as defined in claim 1.

6. The compound according to claim 1 in which $R^{10}$ is a group VI, as defined in claim 1.

7. The compound according to claim 1 in which $R^{10}$ is a group VII, as defined in claim 1.

8. The compound according to claim 1 in which $R^{10}$ is a group VIII, as defined in claim 1.

9. The compound according to claim 1 in which $R^{10}$ is a group IX, as defined in claim 1.

10. The compound according to claim 1 in which $R^{10}$ is a group XI, as defined in claim 1.

11. The compound according to claim 1 in which the moiety $CO_2R^{13}$ is positioned in a para relationship.

12. The compound according to claim 1 in which the moiety $CO_2R^{13}$ is positioned in a meta relationship.

13. The compound according to claim 1, which is selected from the group consisting of:

6-(1,4,4-trimethyl-1,2,3,4-tetrahydroquinolin-6-yl)-naphthalene-2-carboxylic acid methyl ester (11);

3-[4-(1,4,4-trimethyl-1,2,3,4-tetrahydroquinolin-6-yl)-phenyl]-acrylic acid methyl ester (13); and 4-2-[2,4,4-trimethyl-1-(propan-2-yl)-1,4-dihydroquinolin-6-yl]ethynylbenzoic acid, (17);

and isomers thereof;

in free or in salt form.

* * * * *